US008574188B2

(12) United States Patent
Potter et al.

(10) Patent No.: US 8,574,188 B2
(45) Date of Patent: *Nov. 5, 2013

(54) DRUG DELIVERY TECHNOLOGY

(75) Inventors: David Stuart Potter, Cowes (GB);
Charles David Ogilvy Potter, Witney (GB)

(73) Assignee: Glide Pharmaceutical Technologies Limited, Oxfordshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/217,672

(22) Filed: Aug. 25, 2011

(65) Prior Publication Data

US 2011/0313348 A1    Dec. 22, 2011

Related U.S. Application Data

(60) Division of application No. 11/633,804, filed on Dec. 5, 2006, now Pat. No. 8,088,406, which is a continuation of application No. 10/238,415, filed on Sep. 10, 2002, now Pat. No. 7,615,234.

(30) Foreign Application Priority Data

Sep. 11, 2001 (GB) .................................. 0121914.6
Aug. 5, 2002 (GB) .................................. 0218126.1

(51) Int. Cl.
*A61M 31/00* (2006.01)
*A61M 5/30* (2006.01)

(52) U.S. Cl.
USPC .................................. 604/59; 604/57; 604/68

(58) Field of Classification Search
USPC ............ 604/59, 68–72, 117, 93.01, 130–135, 604/181, 187, 218, 225, 227, 232, 234, 235, 604/115
See application file for complete search history.

(56) References Cited

U.S. PATENT DOCUMENTS 1,819,415 A   8/1931   Harris
2,398,644 A   4/1946   Lockhart
(Continued)

FOREIGN PATENT DOCUMENTS

CA   1019638       10/1977
DE   3644984 A1    7/1988
(Continued)

OTHER PUBLICATIONS

United Kingdom Search Report, Application No. GB 0121914.6, dated Jun. 7, 2002.
(Continued)

*Primary Examiner* — Nicholas Lucchesi
*Assistant Examiner* — Leah Stohr
(74) *Attorney, Agent, or Firm* — Nixon & Vanderhye P.C.

(57) ABSTRACT

The invention relates to a novel drug delivery technology. More particularly the invention relates to a method of delivering at least one therapeutic compound or a formulation comprising the at least one therapeutic compound to a patient; to a throwaway or reusable device for delivering at least one therapeutic compound or a formulation comprising the at least one therapeutic compound to a patient in a manner as set out by the method; to a pioneer projectile for use in said method; to formulations for use in said method and to an injectate comprising a pioneer projectile and formulation. It also relates to a disposable component containing either a pioneer projectile or an injectate. The invention also relates to a throwaway or reusable device for delivering at least one therapeutic compound, or a formulation comprising the at least one therapeutic compound (hereafter drug) to a patient, and a method for administering a drug to a patient using said device. It also relates to a packaged drug for use with said device.

31 Claims, 11 Drawing Sheets

(56) References Cited

U.S. PATENT DOCUMENTS

| | | | |
|---|---|---|---|
| 2,752,918 | A | 7/1956 | Uytenbagaart |
| 3,616,758 | A | 11/1971 | Komarov |
| 3,729,003 | A * | 4/1973 | Hurschman ............. 604/138 |
| 3,797,490 | A * | 3/1974 | Hurschman et al. ....... 604/88 |
| 3,901,158 | A | 8/1975 | Ferb |
| 3,948,263 | A | 4/1976 | Drake, Jr. et al. |
| 3,982,536 | A | 9/1976 | Krogseng et al. |
| 4,022,206 | A * | 5/1977 | Hilleman et al. ........... 604/197 |
| 4,059,107 | A | 11/1977 | Iriguchi et al. |
| 4,116,196 | A | 9/1978 | Kaplan et al. |
| 4,326,524 | A | 4/1982 | Drake |
| 4,419,936 | A | 12/1983 | Coates et al. |
| 4,449,982 | A | 5/1984 | Gould, III |
| 4,518,387 | A | 5/1985 | Murphy et al. |
| 4,664,664 | A | 5/1987 | Drake, Jr. |
| 4,790,824 | A | 12/1988 | Morrow et al. |
| 4,808,184 | A | 2/1989 | Tepic |
| 4,863,429 | A | 9/1989 | Baldwin |
| 4,871,094 | A | 10/1989 | Clements et al. |
| 4,968,302 | A | 11/1990 | Schluter et al. |
| 5,092,842 | A | 3/1992 | Bechtold et al. |
| 5,116,313 | A | 5/1992 | McGregor |
| 5,206,024 | A | 4/1993 | Peery et al. |
| 5,354,287 | A | 10/1994 | Wacks |
| 5,360,410 | A | 11/1994 | Wacks |
| 5,542,920 | A | 8/1996 | Cherif Cheikh |
| 5,549,560 | A | 8/1996 | Van de Wijdeven |
| 5,569,189 | A * | 10/1996 | Parsons .................. 604/68 |
| 5,589,167 | A | 12/1996 | Cleland et al. |
| 5,599,302 | A | 2/1997 | Lilley et al. |
| 5,599,309 | A * | 2/1997 | Marshall et al. .......... 604/136 |
| 5,747,058 | A | 5/1998 | Tipton et al. |
| 6,001,385 | A | 12/1999 | Van De Wijdeven |
| 6,102,896 | A | 8/2000 | Roser |
| 6,117,443 | A | 9/2000 | Cherif-Cheikh |
| 6,120,786 | A | 9/2000 | Cherif Cheikh |
| 6,203,521 | B1 | 3/2001 | Menne et al. |
| 6,264,629 | B1 | 7/2001 | Landau |
| 6,331,310 | B1 | 12/2001 | Roser et al. |
| 6,375,971 | B1 | 4/2002 | Hansen |
| 6,586,006 | B2 | 7/2003 | Duffy et al. |
| 6,680,692 | B2 | 1/2004 | Solbach |
| 6,689,093 | B2 | 2/2004 | Landau |
| 6,783,509 | B1 | 8/2004 | Landau et al. |
| 7,615,234 | B2 | 11/2009 | Potter et al. |
| 2004/0248892 | A1 | 12/2004 | Wang |
| 2006/0161111 | A1 | 7/2006 | Potter |
| 2007/0275044 | A1 | 11/2007 | Potter et al. |

FOREIGN PATENT DOCUMENTS

| | | | |
|---|---|---|---|
| DE | 3839287 | A | 5/1990 |
| EP | 0008636 | | 6/1982 |
| EP | 0139286 | | 5/1985 |
| EP | 0119286 | | 12/1987 |
| EP | 0276158 | | 7/1988 |
| EP | 0427457 | A2 | 5/1991 |
| EP | 0 518 416 | A1 | 12/1992 |
| EP | 0518561 | | 12/1992 |
| EP | 0409365 | | 4/1994 |
| EP | 0595508 | | 5/1994 |
| EP | 0666084 | A2 | 8/1995 |
| EP | 0879609 | A2 | 11/1998 |
| FR | 1014881 | | 6/1952 |
| FR | 1049564 | | 12/1953 |
| FR | 2627698 | | 3/1988 |
| FR | 2749764 | A | 12/1997 |
| GB | 993309 | | 5/1965 |
| GB | 2193644 | | 12/1988 |
| GB | 2239180 | | 6/1991 |
| GB | 2365100 | | 2/2002 |
| WO | WO 94/07553 | | 4/1994 |
| WO | WO 94/22423 | | 10/1994 |
| WO | WO 96/40351 | | 12/1996 |
| WO | WO 00/62734 | | 10/2000 |
| WO | WO 02/48654 | A1 | 6/2002 |
| WO | WO 2006082439 | | 8/2006 |

OTHER PUBLICATIONS

United Kingdom Search Report, Application No. GB 0121914.6, dated Aug. 8, 2002.

European Patent Office, Search and Examination Report, Application GB0605772.3, Apr. 26, 2006.

\* cited by examiner

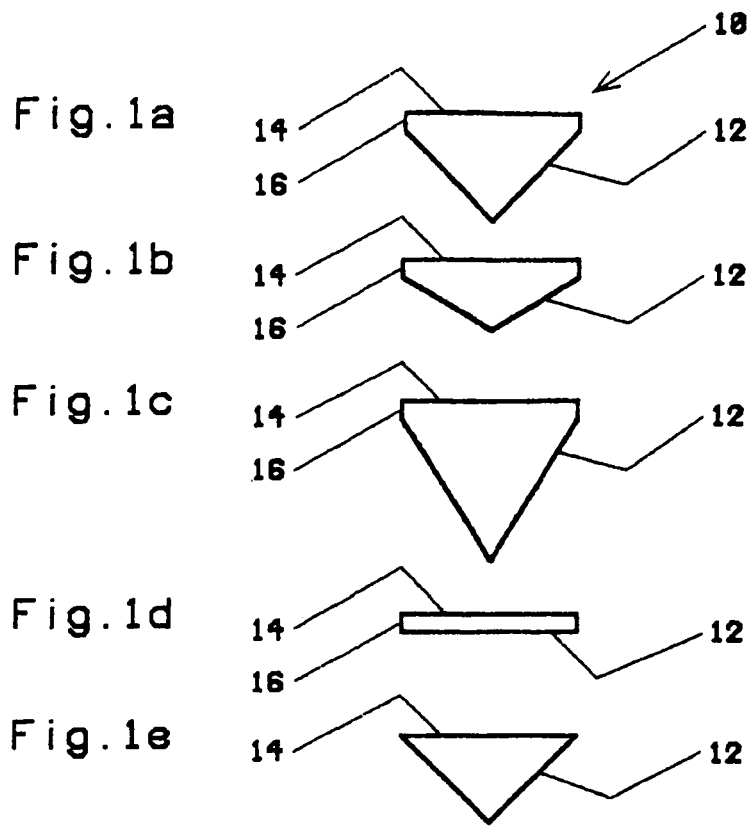
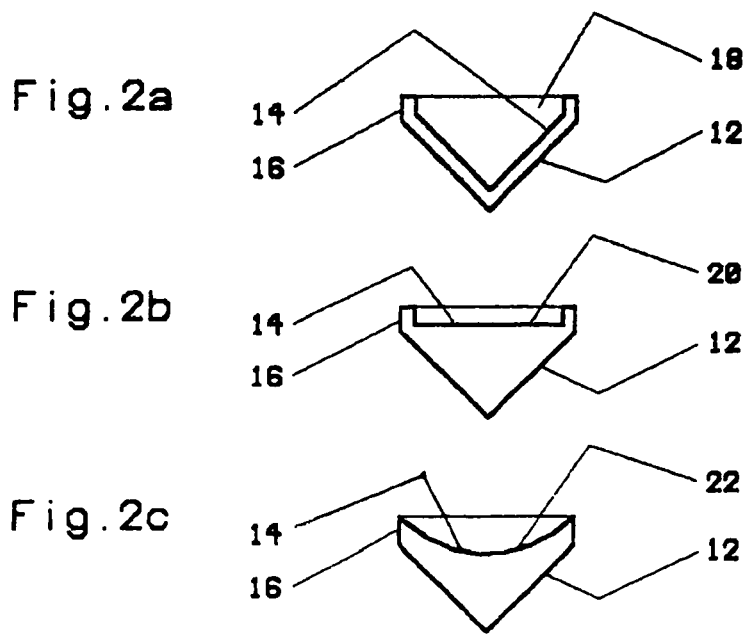

Fig.5b 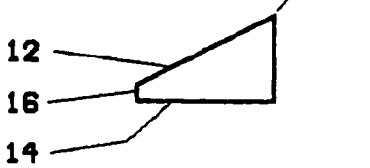  Fig.5c

Fig.6b 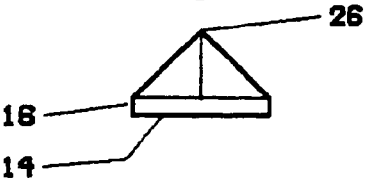  Fig.6c

Fig.7b 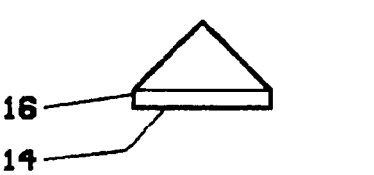 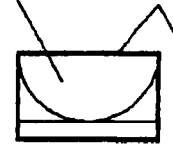 Fig.7c

Fig.8b 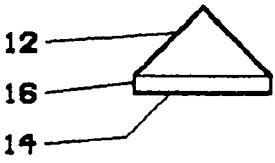  Fig.8c

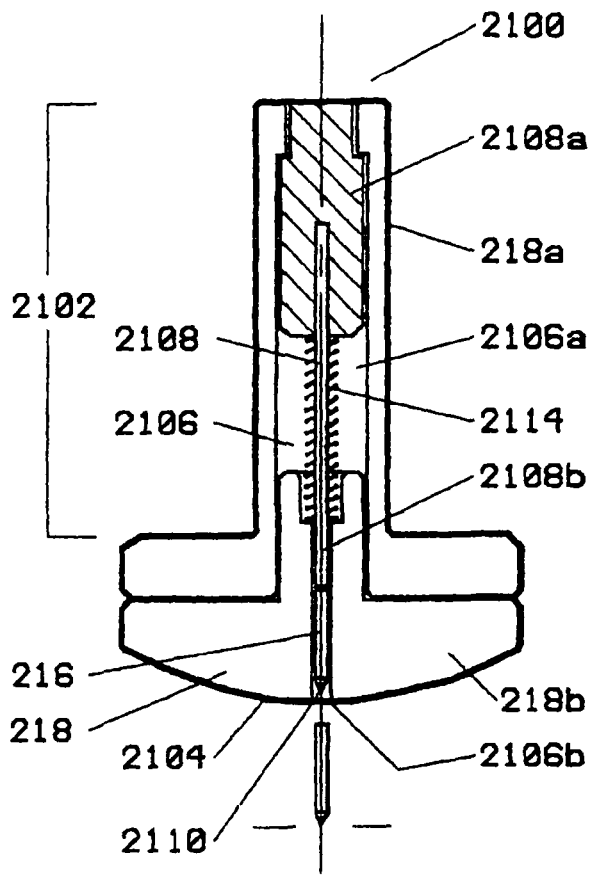
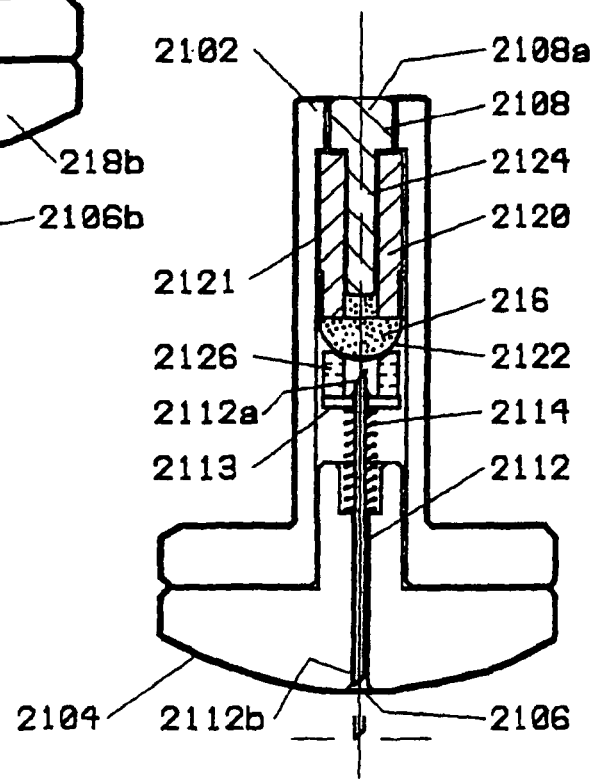

DRUG DELIVERY TECHNOLOGY

This application is a divisional of Ser. No. 11/633,804 (now U.S. Pat. No. 8,088,406), which was filed on Dec. 5, 2006 now U.S. Pat. No. 8,088,406 (published as US 2007-0275044-A1 on Nov. 29, 2007), which is a continuation of Ser. No. 10/238,415 (now U.S. Pat. No. 7,615,234), filed Sep. 10, 2002, and further claims benefit of UK Application No. 0218126.1, filed Aug. 5, 2002 and UK Application No. 0121914.6, filed Sep. 11, 2001, the entire contents of each of which are hereby incorporated by reference.

FIELD OF THE INVENTION

The present invention relates to a novel drug delivery technology. More particularly the invention relates to a method of delivering at least one therapeutic compound or a formulation comprising the at least one therapeutic compound to a patient; to a throwaway or reusable device for delivering at least one therapeutic compound or a formulation comprising the at least one therapeutic compound to a patient in a manner as set out by the method; to a pioneer projectile for use in said method; to formulations for use in said method and to an injectate comprising a pioneer projectile and formulation. It also relates to a disposable component containing either a pioneer projectile or an injectate. The present invention also relates to a throwaway or reusable device for delivering at least one therapeutic compound, or a formulation comprising the at least one therapeutic compound (hereafter drug) to a patient, and a method for administering a drug to a patient using said device. It also relates to a packaged drug for use with said device.

BACKGROUND TO THE INVENTION

One route of administration for therapeutic compounds is through the skin. The skin is also one of the more efficient routes for delivery of a therapeutic compound when compared to other standard delivery routes such as oral or pulmonary delivery.

Administration to the skin is most commonly undertaken using a needle and syringe as a delivery system with the therapeutic compound in a liquid form.

Such a system has a number of associated problems including the pain and fear associated with needles, the fact they are really best suited to injecting liquids which are not necessarily the best way of delivering compounds to a patient and the fact that sharps are left which create a disposal problem.

Drug delivery systems that do not incorporate needles are also used for injecting liquids through the skin and this is achieved by the delivery system creating a very fine, high velocity liquid jet that creates its own hole through the skin. There are however a number of problems with such a method including splash back.

With both these forms of liquid delivery relatively large volumes of liquid are injected which, because they are incompressible, have to tear the tissue apart in order to be accommodated.

However, drug injection through the skin does not have to be achieved with the drug in a standard liquid form. Solid form drugs have been successfully administered with the PowderJect system, which uses a compressed gas source to accelerate powdered drugs to a velocity at which they can penetrate the outer layers of the skin. This system typically employs powdered drug particles of less than 100 microns in diameter, which require a velocity of several hundred meters per second in order to penetrate human tissue. However the system has its own inherent problems such as controlled delivery.

It has also been shown in the past that solid rods or splinters of a therapeutic compound can be pushed, at a relatively low velocity, into the skin without the requirement for a needle although more traditionally these are delivered as implants.

The current transdermal drug delivery techniques can thus be categorised into groups based on the drug form and the velocity of the injection as set out in table 1 below:

TABLE 1

| Drug Injection Velocity | Drug Form | |
| --- | --- | --- |
| | Liquid | Solid |
| High Velocity | Liquid Jet Injector | PowderJect Systems Drug darts |
| Low Velocity | Needle and Syringe | Drug 'Splinters' |

Drug darts are disclosed in a number of publications. WO 96/40351 (American Cyanamid) discloses an implant dart with a head of a solid plastics material which takes the form of a blade and a tubular body that contains one or more sustained release drug delivery implant packages. Flexible stabilizing wings are provided on either side of the dart head which serve as a lock or barb to prevent the dart being pulled out after entry. The dart has on outside diameter of about 7 mm and a length of about 45 mm and is delivered with an injection gun which fires the dart into an animal, but not a human, when a trigger is released. The propulsion mechanism delivers a force sufficient to impart a high accelerating velocity of from 40-60 mph on the dart. To inject the dart at low speed it is necessary to make a small incision in the animal and operate the push bar manually.

U.S. Pat. Nos. 3,948,263 and 4,326,524 also disclose ballistic delivery devices. U.S. Pat. No. 3,948,263 discloses a ballistic implant which is fired from a 0.25 calibre rifle. The projectile exits at about 900 ft/sec and can travel 20-40 ft before implanting into muscle some 1-2 inches beneath the skin. U.S. Pat. No. 4,326,524 discloses a solid dose ballistic projectile formed entirely of a cohesive mixture comprising biologically active material, in the form of grindable solid particles and a binder which is capable of withstanding the stresses imparted on impact. The projectile has a body portion with a diameter of from 4.5 to 7.6 mm, with a conical nose portion with a base diameter smaller than the diameter of the body such that a slight shoulder region is formed between the body and the nose. The end remote from the nose is preferably concave to aid flight.

GB 2365100 is another example of a remote ballistic delivery device which is fired and attains velocities of greater than 500m/s. In contrast to those described above the device is slowed on impact so that it does not enter the body but instead the device's nose is moved back such that a needle enters the body, and a drug is injected. Such a device is not needleless.

CA1019638 discloses a projectile which is launched by a conventional air gun or bow. It comprises a head piece and a shaft, the head piece pierces the animals flesh and the shaft breaks away. In one embodiment the head piece is made of a porous material which retains a liquid drug through capillary action through launch and impact and which releases it by diffusion when it is inserted into the animal. In a second embodiment the head piece takes the form of a hardened cake. To aid penetration a metal or plastics tip may be provided. The drug delivering element remaining in the skin is about 3 mm diameter by 13 mm in length.

U.S. Pat. No. 3,901,158 Ferb discloses a hypodermic projectile which is again fired from a rifle or pistol. It comprises a shatterable front end of plastic or glass which breaks on impact releasing the liquid contents.

None of the described high velocity devices bear any resemblance to the present invention in which the at least one therapeutic compound or a formulation comprising the at least one therapeutic compound is pushed at low velocity from a device which contacts the skin and in which the pioneer projectile is water soluble, lipid soluble or otherwise biodegradable in the human or animal and is furthermore significantly smaller having a width or diameter of less than 3 mm in width, more preferably still less than 2.5 mm through 2 mm and 1.5 mm to about 1 mm in width; a height of less than 10 mm in height, more preferably about 1.5 to 2 mm in height and an aspect ratio of less than 1:8, preferably less than 1:6, more preferably less than 1:4, more preferably still less than 1:3, and most preferably about 1:1.5.

High velocity liquid systems are exemplified by U.S. Pat. No. 116,313 Mc Gregor. Liquid is first ejected from a small orifice in a probe at a very high velocity and pressure which will penetrate the skin and then the main charge of liquid is ejected at a lower velocity into the channel formed by the initial penetration.

EP0139286 (Sumitomo Chemical Co Limited) discloses sustained-release preparations in the form of needle like or bar like shapes, which comprise an active ingredient and a pharmaceutically acceptable biodegradable carrier. The sustained-release preparation can be administered to the body by injection by pushing it through a hollow needle or by implantation.

WO 94/22423 (Bukh Meditec AIS) discloses a drug administration system. The method of parenteral administration comprises administering a drug substance by penetrating the skin or the mucosa of a human or an animal by a body with an appropriately formed solid pharmaceutical composition. The body of the pharmaceutical composition may be needle shaped so as to avoid external penetration equipment. The solid pharmaceutical composition comprises at least one drug substance and has a shape and/or strength to enable penetration. The composition is made by mixing a material, preferably a polymer and optionally a filler with an active drug substance; extruding the mixture to form an elongate body; drying it and forming a pointed end.

U.S. Pat. Nos. 5,542,920, 6,117,443 and 6,120,786 (Cherif Cheikh) all disclose needle-less parenteral introduction devices. A medicament is made in the form of a solid needle having a pointed end that has sufficient structural integrity to penetrate the skin. The needles are less than 2 mm, preferably 0.2 to 0.8 mm, in diameter and 10 to 30 mm in length.

U.S. Pat. No. 6,102,896 (Roser) is primarily directed to a disposable injector device for injecting controlled release water soluble glass needles. It however also recognises that these glass needles, which are about 1 mm in diameter by 10 mm in length and contain a medicament may also be used as pioneer projectiles to produce a low resistance pathway through the tissue along which a liquid suspension (exemplified as a drug in a suspension of PFC fluid) can flow. This document appears the first and only document to recognise that a dissolvable pioneer projectile may be used to enable the introduction of a medicament. It however fails to recognise that it may be used as a general technique for introducing medicaments in other forms. Indeed this is readily apparent from the document in which a dry powdered formulation is made into a non viscous liquid by suspending it in PFC.

SUMMARY OF THE INVENTION

The present invention takes the concept of using a pioneer projection (as disclosed in U.S. Pat. No. 6,102,896) further and follows from the applicants recognition that a pioneer projectile can be used as a means for introducing medicaments in forms other than a free flowing, non viscous liquid.

According to a first aspect of the present invention there is provided a method of delivering at least one therapeutic compound or a formulation containing the at least one therapeutic compound to a human or animal in the form of a needleless injection comprising:

i) Penetrating the skin with a water soluble, lipid soluble or otherwise biodegradable pioneer projectile having a diameter of less than 3 mm which is left in the human or animal; and ii) Introducing directly, or substantially directly, behind the pioneer projectile, the at least one therapeutic compound or the formulation containing the at least one therapeutic compound, which at least one therapeutic compound or the formulation containing the at least one therapeutic compound is provided and delivered in a contained state.

By contained state is meant either:

i) As a liquid contained by a membrane;

ii) As a liquid with a viscosity of at least 5000 centipoises (the viscosity of honey), more particularly at least 50,000 (the consistency of mayonnaise) and most preferably still at least 100,000 (the consistency of peanut butter), such that the liquid has characteristics more akin to a solid than a liquid i.e. they have a definite shape as well as volume (and are not readily free flowing);

iii) As a semi-solid (having a viscosity and rigidity intermediate that of a solid or a liquid);

iv) As a paste (having a soft malleable consistency);

v) As a gel (a liquid dispersed in a solid) which materials can all be considered to have a degree of stiffness; or vi) As a solid (a state in which the matter retains its own shape).

Introducing a medicament in such a contained state has advantages in that splash back and seepage can be avoided and more controlled dosages delivered when compared to a following non viscous liquid formulation. The viscous, semi solid or solid nature of the medicament ensures that the pioneer projectile is pushed to the requisite depth and is followed by the medicament rather than seeping around the sides of the projectile. The semi solid formulations, gels, pastes and solids are also generally more stable than liquid formulations and are more patient compliable.

Furthermore it will be appreciated that by introducing the medicament in a form other than as a non viscous liquid behind a pioneer projectile it is possible to tailor the characteristics of the medicament for optimum pharmacokinetic delivery rather than for penetration.

Similarly the pioneer projectile can be developed to have optimised penetrating capabilities independent of the medicament.

Preferably the pioneer projectile is independent of the at least one therapeutic compound or the formulation containing the at least one therapeutic compound.

Alternatively the pioneer projectile is independent of yet forms an integral part of the at least one therapeutic compound or the formulation containing the at least one therapeutic compound.

Most preferably the pioneer projectile forms a head to the at least one therapeutic compound or the formulation containing the at least one therapeutic compound.

The at least one therapeutic compound or the formulation containing the at least one therapeutic compound can take a number of forms.

In one embodiment the at least one therapeutic compound or the formulation containing the at least one therapeutic compound is a liquid contained in a water soluble, lipid soluble or otherwise biodegradable membrane.

In another embodiment the at least one therapeutic compound or the formulation containing the at least one therapeutic compound is provided in a solid form such as, for example, crystals, particles, granules, beads, rods, discs or a combination thereof.

In yet another embodiment the at least one therapeutic compound or the formulation containing the at least one therapeutic compound is provided as a viscous liquid, semi solid, gel or paste which may be further supported, if desirable, by a water soluble lipid soluble or otherwise biodegradable membrane.

In the method of the invention the skin is penetrated and the therapeutic compound administered at a low velocity. By low velocity is meant less than 100 m/s. Preferably the velocity is less than 10 m/s, more preferably still less than 5 m/s and most preferably in the order of a few m/s.

Since the injectate is pushed at a low velocity rather than fired at a high velocity it is possible to ensure that the dosage is always delivered to the correct (and same) depth under the skin. This means that the system can be used on different skin types and skin locations and the dosage will still be delivered to the same depth.

According to a second aspect of the invention there is provided a method of facilitating the delivery of at least one therapeutic compound or a formulation containing the at least one therapeutic compound to a human or animal as a needleless injection comprising:
 i) Providing a water soluble, lipid soluble or otherwise biodegradable pioneer projectile having a diameter of less than 3 mm capable of penetrating the human or animals skin; and
 ii) Providing directly, or substantially directly, behind the pioneer projectile, the at least one therapeutic compound or the formulation containing the at least one therapeutic compound in a contained state.

The act of pushing the at least one therapeutic compound in the contained state causes the pioneer projectile to penetrate the human or animals skin and the therapeutic compound or the formulation containing the at least one therapeutic compound follows the pioneer projectile and is introduced into the human or animal in the contained state.

The invention also extends to novel pioneer projectiles.

According to a third aspect of the present invention there is provided a water soluble, lipid soluble or otherwise biodegradable pioneer projectile having a diameter of less than 3 mm, and which is capable of penetrating the skin of a human or animal to thereby facilitate the injection of at least one following therapeutic compound or therapeutic compound containing formulation in a contained state, comprising:
 i) A first "penetrating" face which in use penetrates the human or animals skin; and
 ii) Remote from the first face a second "driven" face which in the course of injection is the face upon which a driving force is exerted through the contained therapeutic compound or therapeutic compound containing formulation; characterised in that said pioneer projectile has an aspect ratio (width to height) of less than 1:10.

Because the pioneer projectile has been developed separately of the medication it has been possible to reduce its size from one of at least 10 mm in length to about a few millimeters. It has also been possible to optimise its shape such that it functions as a leading head or tip for a following contained formulation, the two components forming an injectate.

Preferably the pioneer projectile has an aspect ratio of less than 1:8, preferably less than 1:6, more preferably less than 1:4, more preferably still less than 1:3, and most preferably about 1:1.5.

Preferably the pioneer projectile is less than 3 mm in width, more preferably still less than 2.5 mm, through 2 mm and 1.5 mm, to about 1 mm in width.

Preferably the pioneer is less than 10 mm in height, more preferably about 1.5 to 2 mm in height. By reducing the height to a minimum it is possible to maximise the amount of therapeutic compound being injected. In this regard it should be noted that if the combined pioneer projectile and following drug formulation is too long it might not be possible to deliver the drug to the optimum depth.

In one embodiment the pioneer projectile is free of any therapeutic compound. In another embodiment it comprises at least one therapeutic compound. Thus, for example it might be beneficial to include, for example, an antibiotic in the pioneer projectile or have it release a therapeutic compound at a different rate to the formulation in, for example, the case of insulin injections.

The skin penetrating face of the pioneer projectile preferably comprises a cutting element to facilitate entry. This may take the form of a sharp point or an oblique edge. Alternatively the skin penetrating face may be blunt or gently curved.

In one embodiment the face for contacting the therapeutic compound or therapeutic compound containing formulation in a contained state is flat. Alternatively it may be concave or otherwise hollowed to facilitate pushing and formulation containment.

The pioneer projectile may be made of any suitable material. Suitable materials are those hard and rigid enough to facilitate penetration at low velocities. Preferred materials include glassy materials e.g. the sugar glasses as noted in WO 98/41188 which materials are included herein by reference. The term "sugar" thus covers not only disaccharide sugars, such as, trehalose, but also monosaccharide sugars and their non reducing derivatives, such as, sugar alcohols including: mannitol, inositol, xylitol, ribitol and the like, which form a general class of stabilising glass-forming sugars and sugar derivatives. The term "sugar glass" is to be understood as covering not only glasses which are readily and rapidly dissolved in an aqueous environment, such as, trehalose but also sugar glasses in which the sugar molecule has been modified by the attachment of one or more hydrophobic side chains to make the glass more slowly soluble in bodily fluids than the native sugar in order to give controlled release characteristics.

In some circumstances the pioneer projectile may comprise a barrier material over at least the face that contacts the therapeutic compound in a contained state or vice versa such that the respective components will not react with one another.

The invention also extends to novel formulations.

According to a fourth aspect of the present invention there is provided a therapeutic compound or therapeutic compound containing formulation which is held in a contained state and adapted for introduction into a human or animal in the form of a needleless injection behind a water soluble, lipid soluble or otherwise biodegradable pioneer projectile having a diameter of less than 3 mm.

Preferably the formulation comprises less than 50 mg of therapeutic compound in a volume of less than 50 mm$^3$, more preferably less than 10 mg of therapeutic compound in a volume of less than 10 mm$^3$.

The therapeutic compound or therapeutic compound containing formulation may be provided as a liquid contained in water soluble, lipid soluble or otherwise biodegradable membrane.

In an alternative embodiment the therapeutic compound or therapeutic compound containing formulation is provided in a solid form comprising for example crystals, particles, granules, beads, rods, discs or a combination thereof which are generally likely to be more stable than traditional non-viscous liquid formulations with a viscosity similar to that of water e.g. 1 Centipoise or glucose e.g. 500 Centipoises.

In a preferred embodiment the therapeutic compound or therapeutic compound containing formulation is provided as a semi solid, gel or paste. In this form it is particularly patient compliant and the therapeutic compound is generally likely to be more stable than if it were in a traditional non-viscous liquid formulation.

Where the therapeutic compound or therapeutic compound containing formulation is a viscous liquid, it preferably has a viscosity of at least 10,000 Centipoises more preferably at least 50,000 Centipoises and more preferably still at least 100,000 Centipoises.

The formulation may comprise an end piece beyond the therapeutic compound or therapeutic compound which is free of the "active" being injected thus ensuring that the entire therapeutic compound enters the patient in a unit dose rather than risk under or over dosing.

The therapeutic compound or therapeutic compound containing formulation may comprise a plurality of differently formulated elements.

The therapeutic compound or therapeutic compound containing formulation may be packaged in a cap, cartridge, carousel or cassette.

The invention also extends to an injectate comprising a pioneer projectile and a therapeutic compound or therapeutic compound containing formulation.

According to a fifth aspect of the present invention there is provided a needleless injectate for injection comprising:
 a) A water soluble, lipid soluble or otherwise biodegradable pioneer projectile having a diameter of less than 3 mm; and
 b) A therapeutic compound or therapeutic compound containing formulation which is held in a contained state behind the pioneer projectile.

These components are as previously described.

The pioneer projectile and therapeutic compound or therapeutic compound containing formulation may both be water soluble, lipid soluble or otherwise biodegradable to differing degrees.

A barrier may be provided between the pioneer projectile and the therapeutic compound or therapeutic compound containing formulation.

The injectate may be contained/packaged in a cap, cartridge, carousel or cassette optionally together with a means, e.g. an ejector pin, for pushing the injectate out of its container.

Alternatively the pioneer projectile and the therapeutic compound or therapeutic compound containing formulation are contained/packaged in separate caps, cartridges, carousels or cassettes.

The invention also extends to a device for injecting a pioneer projectile and a therapeutic compound or therapeutic compound containing formulation.

According to a sixth aspect of the present invention there is provided a needleless device (60) for injecting a water soluble, lipid soluble or otherwise biodegradable pioneer projectile (10) having a diameter of less than 3 mm and at least one contained therapeutic compound or therapeutic compound containing formulation (42) into a human or animal body, said device comprises a housing (62) containing a mechanism (92) capable of generating a force which will cause a striker (84) to travel along a striker guide (86), said housing having an end face (100) which is in operative communication with a component (72) comprising a casing (74) having an aperture (76) in which is mounted an ejector pin (78) and, therebelow, an injectate (40) comprising a pioneer projectile (10) and a formulation (42) such that in use the striker will contact the ejector pin and the injectate will be pushed out of the casing as a single unit into the human or animal body.

The reference numerals given above are non-limiting but have been included solely for the purpose of assisting the reader.

The term ejector pin is intented to cover a pin, piston, rod or like member which functions to push the injectate from the aperture.

The power source for initiating or assisting the pushing may be a mechanical spring in the form of, for example, a coiled spring or a lever spring. Alternatively, a gas spring might be used or even an electrically powered system. A mechanical spring would allow reuse of the delivery system although this would mean the user has to recharge the spring between administrations. Alternatively, the spring (mechanical or gas) could be pre-charged during manufacture so that it can only be used once and then the whole system would be thrown away. In a reusable device there will be a throw away component containing the pioneer projectile or the pioneer projectile and the therapeutic compound or therapeutic compound containing formulation.

The device preferably incorporates a safety mechanism to avoid accidental actuation. Actuation might be triggered with a push button on the device but preferably would be undertaken by pushing the device against the skin thus ensuring good contact with the skin on actuation.

In a reusable device the reusable component and the throw away component comprise means by which they are connected to one another.

The device may be adapted to inject multiple doses either sequentially or simultaneously. In one embodiment the device comprises a cartridge, carousel or cassette containing a plurality of pioneer projectiles or a plurality of injectates comprising a pioneer projectile and a therapeutic compound or therapeutic compound containing formulation.

In another embodiment the device comprises a cap containing a single pioneer projectile and a single unit dose of the therapeutic compound or therapeutic compound containing formulation.

The various aspects described above give rise to a system having a number of advantages over the prior art delivery methods and some of these are noted in table 2 below:

TABLE 2

| | Benefit | Justification |
|---|---|---|
| 1 | Can use formulations with Increased Product Stability. | Many drugs are more stable in solid form than in a liquid state. A viscous liquid formulation would be more akin to a solid drug in terms of its stability characteristics because of the excipients that can be used |
| 2 | Improved Product Storage | The increased stability with some compounds may allow storage of the final delivery system at room temperature rather than requiring refrigeration |

TABLE 2-continued

| | Benefit | Justification |
|---|---|---|
| 3 | Reduced Risk Of Cross Infection | Without the need for needles there is a reduced risk of blood borne diseases |
| 4 | Small Device Size | Spring, trigger, injectate and piston are the main components required |
| 5 | Cheap Device | A spring is a cheap power source. Small overall number of device components |
| 6 | Reusable Device | The design can allow for the spring to be primed for reuse. Disposable components would be small in terms of size and cost but would include the component holding the injectate or pioneer projectile |
| 7 | Variable Power System | A spring-powered device could allow the tension on the spring to be altered for different skin types and skin positions on the body, if necessary. |
| 8 | Small Skin Response | As experienced with splinters |
| 9 | Quiet Device | Actuation of a spring powered delivery system will be quiet |
| 10 | Easy to Understand Delivery System | Easy to comprehend the forces involved in pushing a foreign body into the skin to a known depth. Easy to measure the physical characteristics required for a 'dose' of injectate of this size |
| 11 | Variable Dose | With a viscous injectate it will be possible to alter the dose injected |
| 12 | Self Injection | With a simple system patients can inject themselves, thus reducing healthcare costs |
| 13 | Controlled Depth Of Penetration Of The Delivered Dose | Pushing the injectate into the skin rather than firing it enables a consistent and controlled depth of penetration in the skin |
| 14 | Large Doses Achievable | Large doses of one or more drugs are achievable by having one or more doses of injectate administered in the same injection |

The concept behind the invention allows for a simple needleless drug delivery device that pushes a drug in a "contained" state.

A semi solid, paste or gel is the preferred form since unlike a non-viscous liquid it would follow the pioneer projectile. (A non-viscous liquid can "splash back" and more easily seep around the track formed by the pioneer projectile.) Its stiffness relative to a non-viscous liquid also means it is easier to push than a non-viscous liquid material. The more solid in nature the better this is. However from a comfort perspective a semi solid or paste or gel is more likely to be patient compliant and dissolve more readily in the body.

The delivery device for delivering such an injectate (pioneer projectile and formulation) could take a number of forms and several such devices are described by way of example.

A first device described is a spring-powered device with the spring, triggering the pushing of a pin. The pin then engages the injectate to push it into the skin with the pin being stopped by either an end stop within the device or by coming into contact with the skin, preferably over a relatively wide area (compared to the injectate) to reduce the force felt on the skin.

If the device is to be reusable then the component holding the injectate might be detached from the rest of the device and thrown away and a new disposable component attached before the next injection. The injection itself would occur in a matter of milliseconds after actuation and would seem instantaneous as far as the user is concerned. Alternatively the formulation might be injected from, for example, a tube and a new pioneer projectile would be required for a further injection.

By way of a further development the needleless device described with reference to the sixth aspect of the invention was further developed with the aim of producing a simple, cheap drug delivery device which is adaptable and able to deliver a drug in the form of not only a needleless injectate but also other forms, such as, for example liquid formulations, and solid drug needles.

This aim is achieved by the provision of a device which is adapted to receive a packaged drug which is slidably mounted in the device such that in use the device is able to push the drug from its packaging, the packaged drug being packaged such that the drug, whatever it's form, can be pushed from its packaging by the device.

It is another and independent aim to package different drug forms for use with such a device.

This aim is achieved by the provision of a packaging adapted to be attached to the device and which comprises a channel housing the drug, and a drive pin or like element for pushing it out when actuated by the device.

There are many possible product applications for such a delivery device and they include therapeutic, prophylactic and diagnostic applications. Applications may be limited to those drugs that are administered in relatively low doses because of the dose limitations for each injection imposed by pushing. However, although each dose may be limited to less than 10 mg or a volume of less than 10 mm$^3$ it would be possible to administer more than one dose either concurrently or sequentially, if larger doses are required.

New laws in many states in the USA are declaring that safety needles must be used for injections whenever possible. These are needles that withdraw into a sheath as the needle is withdrawn from the patient so that the needle tip is not left exposed. This is to avoid the use of a conventional needle which can result in accidental needle stick injuries. A delivery system that either does not require a needle (or that incorporates a needle that retracts) would be beneficial for the US market as well as other parts of the world that will, no doubt, follow the lead of the Americans.

Particular applications where the technology might be very well suited include:

Vaccines:—Vaccinations are one of the common reasons for people to need an injection and many people would rather risk catching a disease than have to be injected with a standard needle and syringe. Children in particular can often have a needle phobia. Therefore a system that either does not incorporate a needle (or the needle is never seen by the patient) might help compliance with vaccines. In third world countries there is a great need for delivery systems for vaccines that do not involve needles. An added advantage of the new delivery system is that using a non liquid dose therapeutic compound should assist stability of the active compounds and therefore the cold chain storage requirements for the vaccine may be avoided.

Acute Emergencies:—The device is very quick and easy to use and therefore well suited for self administration as well as administration by an untrained assistant. There are a number of drugs, such as glucagon (hypoglycaemia), migraine treatments or adrenalin (anaphylactic shock) that are required when the patient may not be in a suitable condition to undertake the injection themselves. Glucagon and some of the migraine treatments are normally supplied as a powder that have to be made up with the diluent before the injection which means that they are not suitable for administration by an untrained assistant. In addition, the patient may, or may not be in a fit state to make up the drug let alone administer it. The present device would enable these and similar drugs to be administered in solid dosage form.

Diabetes:—Millions of people worldwide have to inject insulin either daily or several times a day. Most have to use a needle and syringe although new delivery systems such as inhalers and insulin pumps are becoming more popular. The advantage of the new delivery system is that several different types of insulin can be administered in a solid dose form at one time. This can be done by having two or more short pieces of different insulin formulations in e.g. a drug cassette. This could allow a short as well as a long acting insulin to be injected at the same time and thus reduce the requirement for multiple injections throughout the day.

Although the applications above have been highlighted, the technology is suitable for administering many drugs that are required at the dosage levels capable of being delivered by the system.

According to a seventh aspect of the present invention there is provided a drug delivery device (210) comprising:
i) a housing (212);
ii) a means (214) for generating a force capable of pushing a drug (216) from a packaging (218) into a human or animal body;
iii) a means (220) for transmitting said force to push the drug (216) from the packaging (218) into the human or animal body; and
iv) a means (238, 242b) for triggering the device.

The numbers are again included for illustrative purposes and are not to be construed as limiting.

Such a device can be a reusable device which further comprises a means (222) for receiving a packaged drug (2100); and a means (224) for priming the device.

Alternatively the device can be a single use device in which case the packaged drug (2100) will be an integral part of the device. Such a device can be provided in a pre primed form which just needs triggering or in a form requiring it to be primed.

A device according to the invention has a number of advantages compared to current needle free devices.

It comprises a small number of components and is therefore cheap to manufacture and assemble. It is also relatively small (currently the same size as a dry marker pen).

In a preferred embodiment of the device, it can only be actuated by inserting a packaged drug and pushing the skin tensioning end of the packaged drug against a solid object. The priming and actuation of the device by pushing the end of the device against the skin ensures that there is a reliable and consistent contact and tensioning of the skin on delivery of the drug. Additionally, by setting the device such that the force required to actuate it is from, for example, 20-30 Newton the force will be too high for a patient to accidentally actuate the device without pushing it firmly against the body's tensioned skin, thereby providing a significant safety feature.

A spring and cap arrangement makes it possible to adjust the actuation force by altering the tension on the spring. By screwing the cap further onto the upper barrel the spring is tensioned and by unscrewing it the force can be reduced. Alternatively, instead of a coil spring as the main power source, the device could incorporate any other type of mechanical spring or a gas spring. In an alternative embodiment the spring could be pre-tensioned during manufacture to avoid having to tension the spring during the drug administration. This would result in a single use device in which case the packaged drug would most likely be an integral part of the device.

The velocity of the impact hammer during administration of the therapeutic agent is less than 20 m/s, more preferably less than 10 m/s, more preferably still less than 5 m/s and most preferably in the order of 0.1-2 m/s. The skilled man will appreciate that the actual speed may vary with the mass of the impact hammer and thus the impact imparted on the delivery dose. As a consequence the therapeutic agent is delivered by a pushing action from the end of the packaged drug rather than by a firing action (as would be the case with a bullet leaving the barrel of a gun).

To ensure that the device actuates automatically when the correct force is applied the hammer has a shaped shoulder region which engages a correspondingly shaped surface in a wall separating the upper and lower barrels. The device will actuate only when the substantially frustoconical sections fully engage. This will be at the same main spring tension every administration and if the administration is aborted before the frustoconical sections engage then the packaged drug can be removed safely without leaving the device primed.

In a preferred embodiment the device can't be primed until the packaged drug is attached thereto since it is the packaged drug that acts against the piston in the device to cause the spring to be tensioned. This makes the device particularly safe. It also means it can't be actuated when not loaded such that an operator can't use the device in a belief they are providing an injection.

In the case of a reusable device a stewing spring returns the impact hammer into it's non axially aligned position at the end of each administration.

Furthermore, because the reusable components of the system (all components except those of the packaged drug) do not come into contact with the target tissue for the drug administration they do need to be sterile.

All components apart from the springs can be moulded making the device cheap to manufacture and the limited number of parts and their ease of assembly keeps assembling costs to a minimum.

A range of custom packaged drugs will fit the delivery device but patients will not be able to easily introduce their own therapeutic compounds into the drug cassettes (as can be done with a needle and syringe).

The device is suitable for both human and veterinary applications.

The device is particularly suitable for self administration of drugs and requires minimal training.

According to an eighth and related aspect of the invention there is provided a packaged drug (2100), for use with a drug delivery device, comprising a packaging (218) containing a drug (216), said packaging (218) comprising a housing (218a, 218b) having a channel (2106) running there through and in which is disposed a drive pin or other element (2108), a skin piercing means (2110; 2112), and the drug (216), said housing (218a, 218b) comprising
i) a region (2102) allowing the packaged drug (2100) to be slidably mounted to the drug delivery device (210); and
ii) an end (2104) adapted to engage and tension the skin.

In the case of a drug splinter the skin piercing means and the drug may be one of the same.

Preferably the drug is disposed between the drive pin and the skin piercing means.

Preferably the packaged drug takes the form of a disposable end cap, cartridge, cassette or carousel, containing a single or multiple doses of the drug.

Preferably the region for engaging the packaged drug to the drug delivery device in a slidable manner additionally comprises a means for positively locking it to the device such that it can still slide within the device but will not fall out under gravity. Such a means might be a sprung pin or spigot which exerts a frictional force against the device or a mechanism whereby the packaged drug is inserted in a particular orientation and turned so that it is precluded from being removed unless it is turned back into the position in which it was allowed to enter.

In a first embodiment the packaged drug houses either a pioneer projectile in combination with a drug in a contained state, more preferably a solid, or a drug splinter (a single solid entity).

In a second embodiment the piercing means comprises a needle with two sharp ends, one for puncturing the skin and the other for puncturing a membrane of a receptacle containing the drug, the drug being released into the needle from where it drains out into the body through the needle. The drug is preferably a liquid and is contained in the receptacle which is disposed in the channel. Advantageous features of the device include a spacer between the membrane piercing end of the needle and the membrane of the drug containing receptacle to prevent the needle coming into contact with the membrane prior to actuation. The spacer is either resilient or compressible and may be supported by a plate attached to the needle. The receptacle is preferably sealed by the drive pin or other like element.

In a third embodiment the packaged drug may contain a drug in any state (e.g. solid, semi solid or liquid), the actuation of the device causing, in a two step operation, first the entry of a pioneer projectile and only then the release of the drug from a thin walled tube. Release of the drug may optionally require the breaking of a membrane supporting the drug in the tube.

In a variation of this embodiment the pioneer projectile, which is located immediately in front of the thin tube, could be replaced by a retractable needle tip which is, or is integral with, the thin walled tube. As per embodiment 1 and 2 described above, the thin walled tube could have a compression spring or other resilient member associated therewith to withdraw the thin walled tube following the injection.

A particularly clever feature of this embodiment is the form of the drive pin or element which has a plurality of flexible or frangible arms, in the embodiment illustrated two, extending from its main body. These arms extend outwards (splay) when they ride over a ramped surface provided on the housing, are forced away from the body, and ride over a lip on the tube as a consequence of the flex or frangibility. In consequence the body of the drive pin or element can move down the tube. This arrangement facilitates a two step operation whereby in a first step the drive pin or element acts on the tube causing it to move and push the pioneer projectile into the skin, and then, and only when the first step is complete, the arms are caused to splay and/or snap thereby allowing the drive pin body to push the drug contents from the tube. In the case where the arms are frangible the arms will snap off as a result of an area of weakness formed about the shoulder region and fall into a cavity about the ramped region. A frangible system has two advantages: firstly it should ensure full injection occurs, and secondly it will mean the packaged drug can't be re-used. The ramp is preferably "circular" in design, taking the form of a frustoconical surface. This has the advantage that it can be easily moulded and does not require the arms to be orientated for contact.

Depending on the diameter of the thin walled tube and the viscosity of the therapeutic compound, the thin walled tube may need to be sealed, or partially sealed to avoid premature loss of the drug. However the action of the drive pin body will be sufficient to break any seal allowing the drug to be released and pushed into the patient.

An advantage of the packaged drugs exemplified is their small cheap sub-assembly. They are also easy to handle and place into the device prior to administration. Their size also facilitates easy storage in, for example, refrigerators.

The packaged drug may be sealed in a foil pouch or the like to prevent ingress of, for example, moisture, oxygen, light, bacteria or other drug degrading or contaminating agents.

In those embodiments having a pioneer projectile the tip will, in most instances, be positioned a few millimeters from the end of the drug cassette so that it is moving when it strikes the target tissue.

Preferably the end adapted to engage and tension the skin comprises one or more projections about the channel exit, most preferably in the form of an annular ring, as such an arrangement most effectively tensions the skin.

A retention system may advantageously be employed to hold the drug and pioneer projectile in place in the channel. This might be achieved by, for example, extruding or moulding the drug and/or pioneer projectile with a number of small splines or other features along their outer surface. These splines or other features would provide a frictional fit but would not prohibit the drug from being administered. Alternatively, the channel of the packaging might have a small feature, such as, for example, a retaining bump or other projection over which the pioneer projectile and drug have to be pushed.

A tamper or use evident seal or other indicator means may additionally be placed over the top end of the packaged drug so that when e.g. the seal is broken it is obvious that the packaged drug has not been interfered with and/or is spent.

Additionally or alternatively a seal may be place over the exit of the channel of the packaged drug. It would be preferable to remove this seal prior to administration of the drug but it would best be designed such that the administration could be carried out through the seal just in case it wasn't removed by the user.

According to yet a further aspect of the invention there is provided a method of delivering a drug to a human or animal using a device and/or packaged drug according to the invention.

The various aspects of the invention will now be described, by way of example only, with reference to the following Figures and Examples.

BRIEF DESCRIPTION OF THE DRAWINGS

FIG. 1*a-e* are embodiments of pioneer projectiles of varying shapes and sizes;

FIG. 2*a-c* are embodiments of pioneer projectiles with hollow driven faces;

FIG. 5*a-c* are a plan view, side elevation and end elevation respectively of a pioneer projectile with an oblique cutting edge;

FIG. 6*a-c* are a plan view, side elevation and end elevation respectively of a pioneer projectile with a central piercing point and faceted sides;

FIG. 7*a-c* are a plan view, side elevation and end elevation respectively of a pioneer projectile with a central cutting edge;

FIG. 8*a-c* are a plan view, side elevation and end elevation respectively of a pioneer projectile with a central piercing point;

FIGS. 18a, b, and c illustrate a device substantially similar to the device illustrated in FIG. 17 in:

Figure 21:
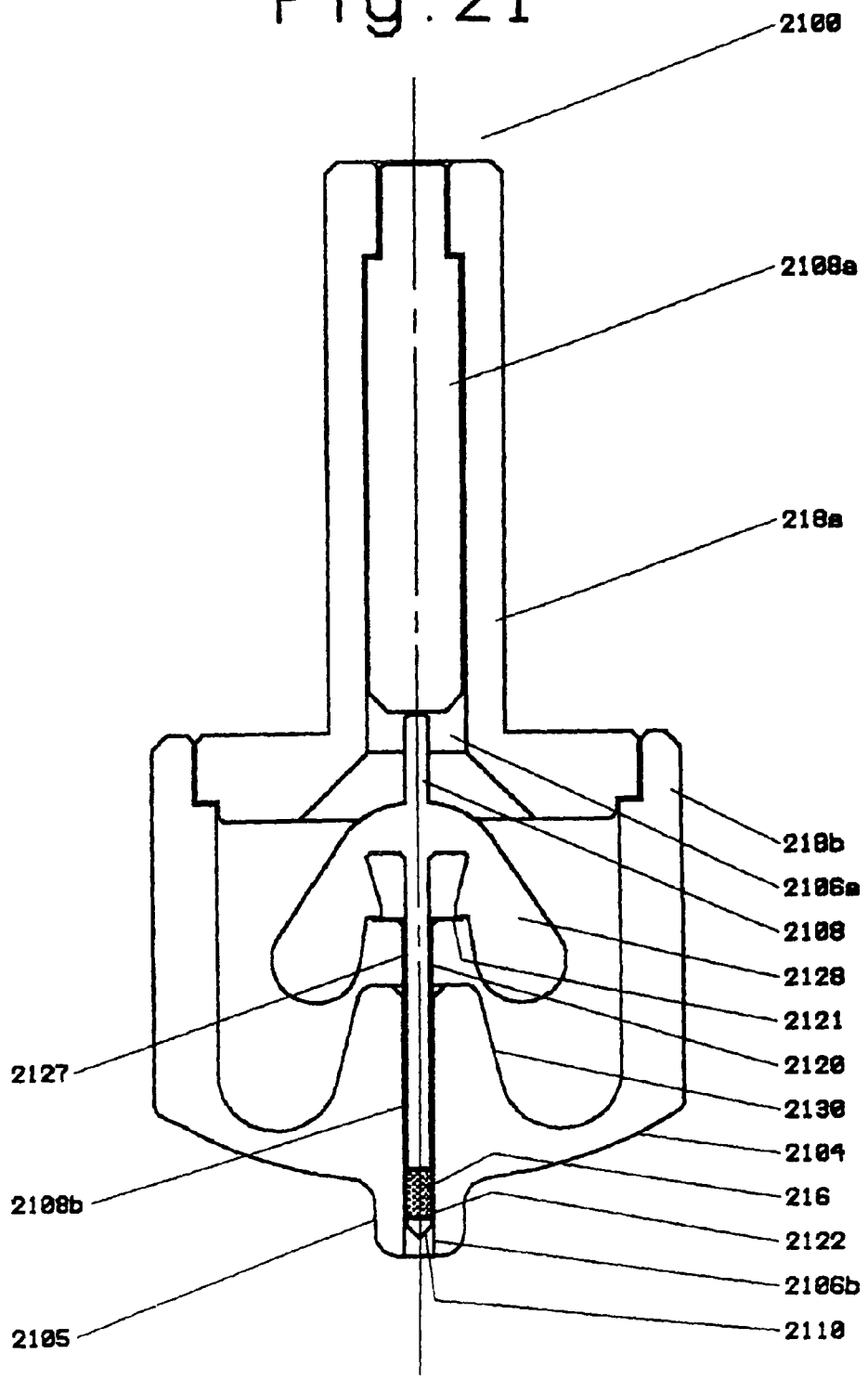

a) its assembled form b) at the point where it is fully primed and about to self actuate; and c) in its post actuation position;

FIG. 19 is a packaged drug according to one aspect of the invention in which the drug is in a solid or otherwise contained form and follows a pioneer projectile;

FIG. 20 is a packaged drug according to another aspect of the invention in which the drug is in a liquid form and is released and injected via a retractable needle; and FIG. 21 is a packaged drug according to yet a further aspect of the invention in which the packaging is adapted to hold a drug in a solid or liquid form and in which the end of the packaging is modified to be particularly well adapted to skin tensioning.

DETAILED DESCRIPTION

Referring to the drawings, FIG. 1a is a side elevation of a pioneer projectile 10 according to one aspect of the present invention. It is made of a crystalline or amorphous material, preferably a glassy material, (e.g. a sugar glass such as trehalose, palatinit, glucopyranosyl sorbitol, glucopyranosyl mannitol, lactitol or monosaccharide alcohols such as mannitol or inositol) which is water-soluble and dissolves in the body. The material may include a hardening agent, such as, for example, povidone (pvp). The pioneer projectile comprises a penetrating face 12 comprising one of more facets, which has a central point, one or more guiding faces 16 for guiding the pioneer projectile within a central aperture or chamber of a needleless device for injecting an injectate (comprising the pioneer projectile and a formulation) thus ensuring the pioneer projectile meets the skin at a suitable angle to aid penetration, and a driven face 14. The pioneer projectile has an aspect ratio (width W to height H) of about 1.25:1.

The pioneer projectile can however take a number of forms and some further embodiments are illustrated in FIG. 1b-d, FIG. 2a-2c, FIG. 3a-d, FIG. 4a-c, FIG. 5a-c, FIG. 6a-c; FIG. 7a-c and FIG. 8a-c.

Briefly: FIG. 1b illustrates a pioneer projectile with a very small aspect ratio of about 1:0.5; FIG. 1c illustrates a pioneer projectile with an aspect ratio of about 1:2; FIG. 1d illustrates a pioneer projectile with a blunt and planar penetrating face 12, and an aspect ratio of about 1:0.2; and FIG. 1e illustrates a pioneer projectile which does not have a guiding face 16 but consists of a penetrating face 12 and a driven face 14.

FIGS. 2a to 2c illustrate variations in the driven face 14. Thus in FIG. 2a the driven face is completely hollowed forming a void 18 which can hold, at least in part, at least one therapeutic compound or compound containing formulation. In FIG. 2b the hollow 18 has a flat bottom 20 and in FIG. 2c it has a concave bottom 22.

Of course, the penetrating face 12 need not have a central point and FIGS. 3a-d, and 4a-c illustrate embodiments in which the pioneer projectiles have an oblique cutting edge 24.

Figure 3A:
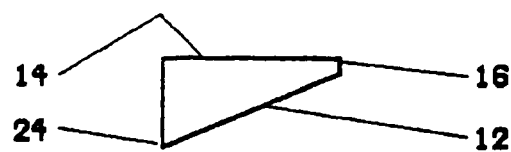
FIG. 3*a-d* are embodiments of pioneer projectiles with an oblique cutting edge.
Figure 3B:
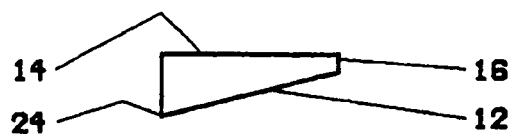
Figure 3C:
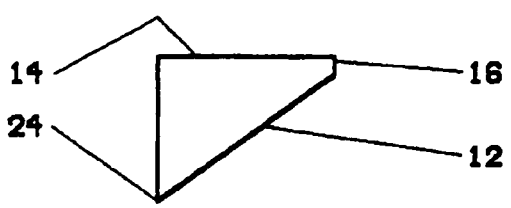
Figure 3D:
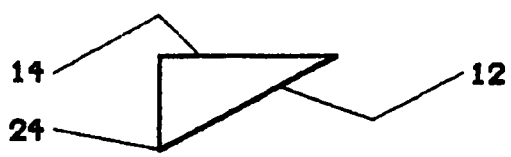
Figure 4A:
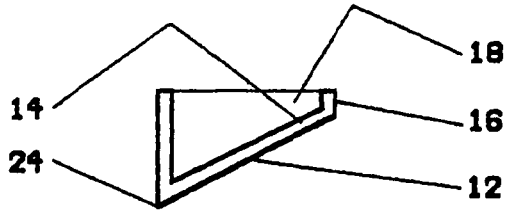
FIG. 4*a-c* are embodiments of pioneer projectiles with an oblique cutting edge and hollow driven faces.
Figure 4B:
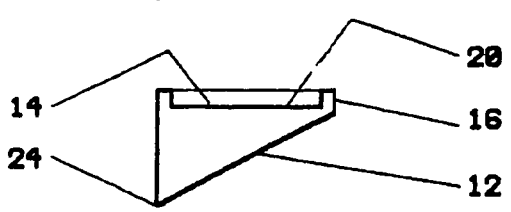
Figure 4C:
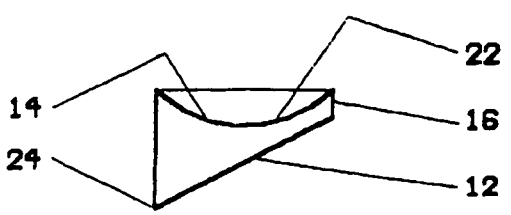
Figure 5A:
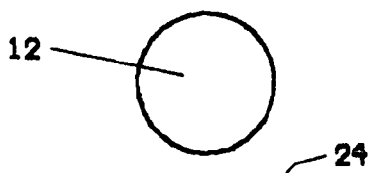

The shape of the penetrating face can, as noted above, take a number of forms as exemplified with reference to FIGS. 5-8. In each of these Figs a) is a plan view; b) is a side elevation and c) is an end elevation. Thus:

In FIG. 5 the pioneer projectile is circular in x-section (FIG. 5a), has an oblique cutting edge 24 (FIG. 5b), and a planar penetrating face 12 (FIG. 5c).

Figure 6A:
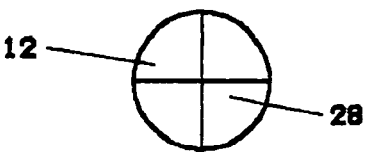

In FIG. 6 the pioneer projectile is circular in x-section (FIG. 6a), has a central point 26 (FIG. 6b), and four facets 28 making up the penetrating face 12 (FIG. 6c).

Figure 7A:

In FIG. 7 the pioneer projectile is circular in x-section (FIG. 7a), has a central cutting edge 30 (FIG. 7b), and two facets 28 making up the penetrating face 12 (FIG. 7c).

Figure 8A:
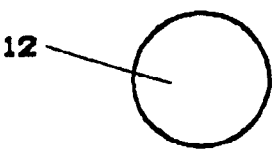

In FIG. 8 the pioneer projectile is circular in x-section (FIG. 8a), has a conical penetrating face (FIG. 8b), culminating in a point 30 and a penetrating face 12 (FIG. 8c).

Of course the pioneer projectile need not be circular in cross section but could be, for example, three sided (triangular), four sided (square) or indeed any other suitable shape.

A pioneer projectile might be manufactured in a number of ways such as by moulding, extrusion or sectioning a rod of the material.

Preferably the pioneer projectile will dissolve in the tissue in a matter of minutes or hours depending on the material used.

The pioneer projectile together with at least one therapeutic compound or formulation forms an injectate.

The physical characteristics of the formulation are very important to ensure that the injectate can be administered to the skin in a reliable and repeatable manner The formulation could take a number of forms:

In one embodiment it might take the form of a paste. This can be achieved by mixing the active drug with the appropriate excipients to end up with consistency, say, like toothpaste. The excipients would obviously need to maintain the active ingredient in a condition such that it was still active during manufacture, storage and administration.

In other embodiments the formulation will be a semi solid, gel, solid or contained liquid.

The therapeutic component of the formulation might be present in one or more of the following formats:

1. Pure drug;
2. With excipients to alter the physical characteristic of the material;
3. With excipients to bulk out the active ingredient;
4. With excipients to buffer the active ingredient;
5. With excipients to change the release profile of the active ingredient; and
6. As a mixture of more than one therapeutic compound.

The formulation can be designed to give the desired release profile for the application. This might involve either a sustained release formulation or a quick dissolving formulation for immediate release into the body. In some cases, such as for the administration of insulin, a formulation might be required that provides an immediate release of some of the therapeutic compound and then a sustained release of another component in the formulation. This might for example be achieved by having the formulation in a plurality of parts or by incorporating a medicament into the pioneer projectile.

Alternatively the therapeutic compound might be formulated as small beads. A number of the beads could be lined up in the device behind a pioneer projectile. On actuation of the device the pioneer projectile pierces the skin and the beads are pushed into the skin behind the pioneer projectile.

The therapeutic component of the formulation must of course not react with the material used for the pioneer projectile or the materials used in the delivery system.

FIGS. 9 to 15 are some embodiments illustrating injectates and formulations of the invention.

Figure 9:
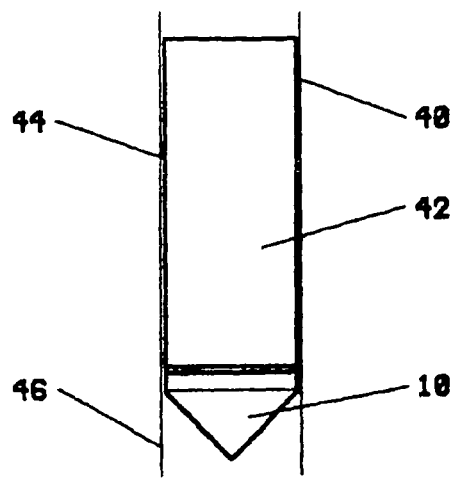
FIG. 9 is one embodiment of an injectate of the invention shown housed in a support or device chamber.

In FIG. 9 an injectate 40 comprises a pioneer projectile 10 and a formulation 42. The formulation is in a contained state supported by its own viscosity or a membrane 44. The formulation is thus a contained liquid or a solid. The injectate may be self-supporting or contained in an optional support 46 which may be a chamber 76 of a device or a throwaway component.

Figure 10:
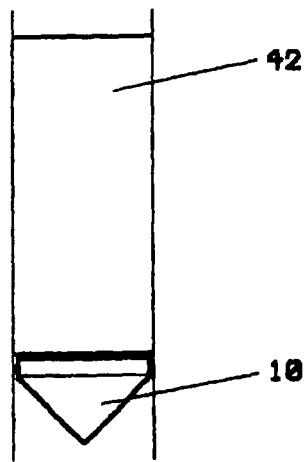
FIG. 10 is another embodiment of an injectate of the invention shown housed in a support or device chamber.

In FIG. 10 the formulation is a high viscosity liquid, gel, paste or semi-solid.

Figure 11:
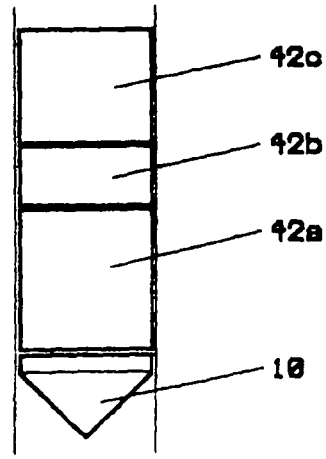
FIG. 11 is another embodiment of an injectate of the invention shown housed in a support or device chamber.

FIG. 11 illustrates an injectate comprising a plurality of different formulations 42a, 42b and 42c. These could be formulations with different release profiles or different active ingredients, for example combination therapies. Though not illustrated there could be membranes between the components e.g. lipid soluble membranes between water-soluble formulations and or an end piece.

Figure 12:
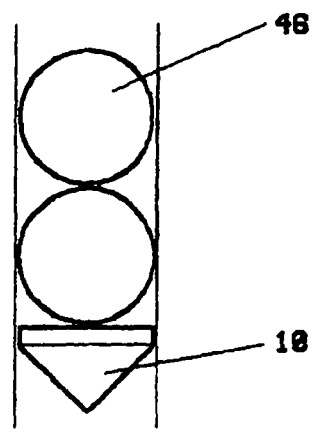
FIG. 12 is another embodiment of an injectate of the invention shown housed in a support or device chamber.
Figure 13:
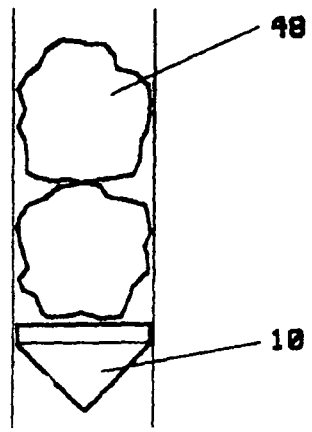
FIG. 13 is another embodiment of an injectate of the invention shown housed in a support or device chamber.
Figure 14:
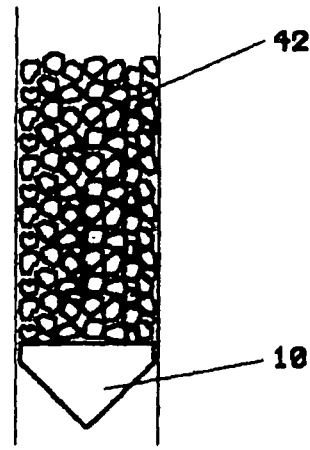
FIG. 14 is another embodiment of an injectate of the invention shown housed in a support or device chamber.

FIGS. 12, 13 and 14 illustrate injectates with different solid formulations. In FIG. 12 the solid formulation takes the form of beads 46. In FIGS. 13 and 14 they are granules, particles or crystals 48.

Figure 15:
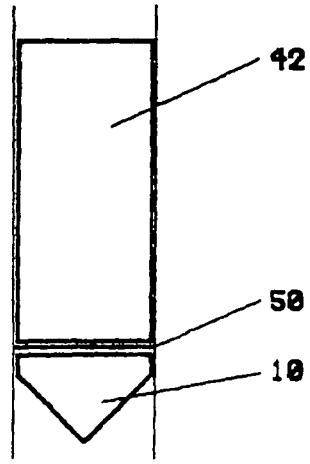
FIG. 15 is another embodiment of an injectate of the invention shown housed in a support or device chamber.

In FIG. 15 a barrier 50 is shown between the formulation 42 and the pioneer projectile 10.

The skilled man will of course realise that the features illustrated with reference to one embodiment could easily be applied to other embodiments.

An injectate will be introduced into a human or animal using a device that injects the injectate in a needleless manner.

Figure 16:
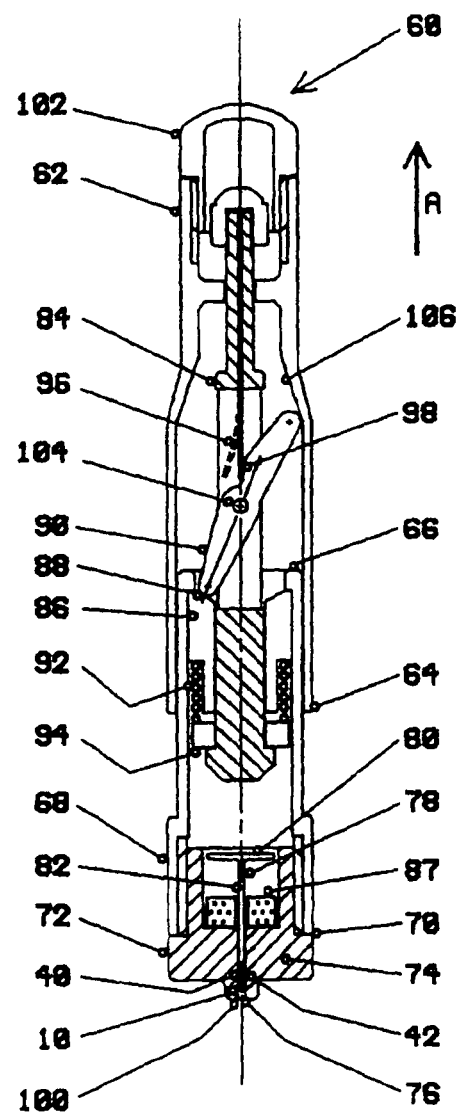
FIG. 16 is cross sectional view of a delivery device of the invention.

One such device is illustrated by way of example only in FIG. 16.

The needleless injection device 60 is shown in the primed position. It comprises an outer housing or holder 62 the lowermost end 64 of which is slidably mounted over the uppermost end 66 of an innermost casing 68.

At the lowermost end 70 of innermost casing 68 is fitted a disposable component 72 such as, for example, a drug cassette. The disposable component comprises a casing 74 having a central aperture or chamber 76 in which is mounted the injectate 40 comprising the pioneer projectile 10 and the formulate 42. A large headed ejector pin 78 comprising a flat head 80 and an elongate body 82 is positioned over the injectate 40 so that when the ejector pin is contacted, in use, by a striker 84 it is pushed along the aperture or chamber 76 and out into the patient. A resilient member 87, such as a rubber block urges the ejector pin back a little after injection.

The disposable component 72 is loaded into the needleless injection device, by for example, screwing it into the lowermost end 70 of the inner housing 68.

Mounted within the innermost housing 68 is a striker guide 86 having a surface 88 which maintains a detent 90 in the loaded position (shown) and houses an actuating mechanism or spring 92 and spring follower 94.

The disposable component 72 is shaped such that when it is in contact with the skin it pre-tensions it prior to actuation. This ensures that the dosage will penetrate the skin rather than just stretch the skin.

The injector pin 78 is designed to push the injectate beyond the end of the device by up to (say) 2.5 mm. This means that the end of the injector pin (which preferably has the same profile and diameter as the end of the pioneer projectile) might just penetrate the skin but it would ensure that the injectate has been fully administered into the skin.

Prior to actuation, the tip of the injectate might be in contact with the skin. However, it is preferred that the tip is a few millimeters away from the skin prior to actuation. This ensures that the injectate is moving when it impacts the skin and also ensures that the tip of the injectate does not start to dissolve, and therefore soften the tip, with any moisture from the skin surface when the device is placed on the skin.

To use the device 60 the outer most casing is retracted (pulled in the direction of arrow A) so that it slides against the innermost housing 68. This action causes the spring 92 to be compressed, and the detent to be moved from a vertical position to the position shown where it is held stable against surface 88. In the process a quill spring 96 stabilises the detent by abutting against a surface 98. Once loaded the disposable component, is screwed into the end 70 of the innermost housing 68 of the device 60.

The injector pin 78 that pushes the injectate into the skin is preferably, (but not necessarily) in contact with the injectate prior to actuation.

To actuate the device a user, for example, grips the device around the outer housing 62 with their thumb over the end cap 102. The end face 100 of the disposable component 72 is positioned against a patient's skin, which should be held taught, and the outer housing 62 is pushed in a direction away from arrow A. This action causes the outermost casing to slide over the inner housing 68. As it does so the detent is caused to rotate about it's axle 104 as a result of the detent riding up inclined wall 106. This forces the quill spring 96 out (as shown by the broken line). When the detent reaches a vertical position the coil spring releases its stored energy and assists in ensuring the striker 84 travels along the striker guide 86 until it contacts the head 80 of the ejector pin 78 with a force that causes the injectate 40 to pierce the skin. The ejector pin 78 continues to push the formulation 42 into the patient to the required depth, which is determined by the length of the injectate and the extent to which it is pushed by the ejector pin 78. The rubber stop 87 is squashed by the ejector pin head 80 during delivery of the injectate but the elastic properties of the rubber stop 87 enable the tip of the ejector pin to be withdrawn into the disposable component 72 of the device.

Injection Sites

The injectate could potentially be injected in a wide number of sites across the human or animal body. The easiest direction to administer the injectate is perpendicular to the skin and so with most skin sites this would mean penetrating the epidermis into the dermis and, depending on the skin thickness, into the subcutaneous layers or muscle. The 'best' injection sites might therefore be those where there is the smallest density of nerve endings to avoid any pain that might be associated with the injection. This might include injections to the back or to the lobe of the ear.

Alternatively, injection sites might include those with a thicker epidermis so that the injectate does not penetrate into the dermis where the nerve endings are located. The injectate might be injected obliquely into the skin so that it is located totally in the epidermis. The same result might be achieved by injection into a fold of skin that has been pinched.

The elastic properties of the skin can be employed to seal the skin after the injectate has been administered, as is often the case with splinters. This ensures the drug does not leak from the skin as it dissolves.

The most likely area of the body for drug administration with this technology is the stomach because of the high fat content and easy accessibility for self-administration. An alternative might be the thigh although this is often less accessible if the recipient is wearing trousers.

Product Applications

There are many possible product applications for this technology because of the doses that are achievable including therapeutic, prophylactic and diagnostic applications. Illustrative examples include, but are not limited to:

Conventional Vaccines—first and third world applications or veterinary applications;
Insulin;
Migraine Treatments; and
Hormones.

The term "at least one therapeutic compound or a formulation containing at least one therapeutic compound" as used in this application is intended to cover prophylactic and diagnostic applications as well as therapeutic applications.

The maximum dose that could be delivered using the technique will depend upon a number of factors. However, an injectate with an overall length of approximately 4.0 mm and a diameter of approximately 1.0 mm (similar to a 19G venflon) would be sufficient to allow a dose of approximately 2 mg of a standard therapeutic in one administration. This magnitude of dose would be suitable for each of the applications exemplified above. If several doses of injectate are delivered simultaneously then there is the potential for an even larger number of applications.

Delivery of the injectate will be very quick and any pain associated with the delivery technique should not be any worse than a needle of similar dimensions. If the delivery technique were painful then it would be possible to anaesthetise the tissue prior to the injection. To avoid needles then this anaesthetic might be given with a patch, a spray or a cream.

Figure 17:
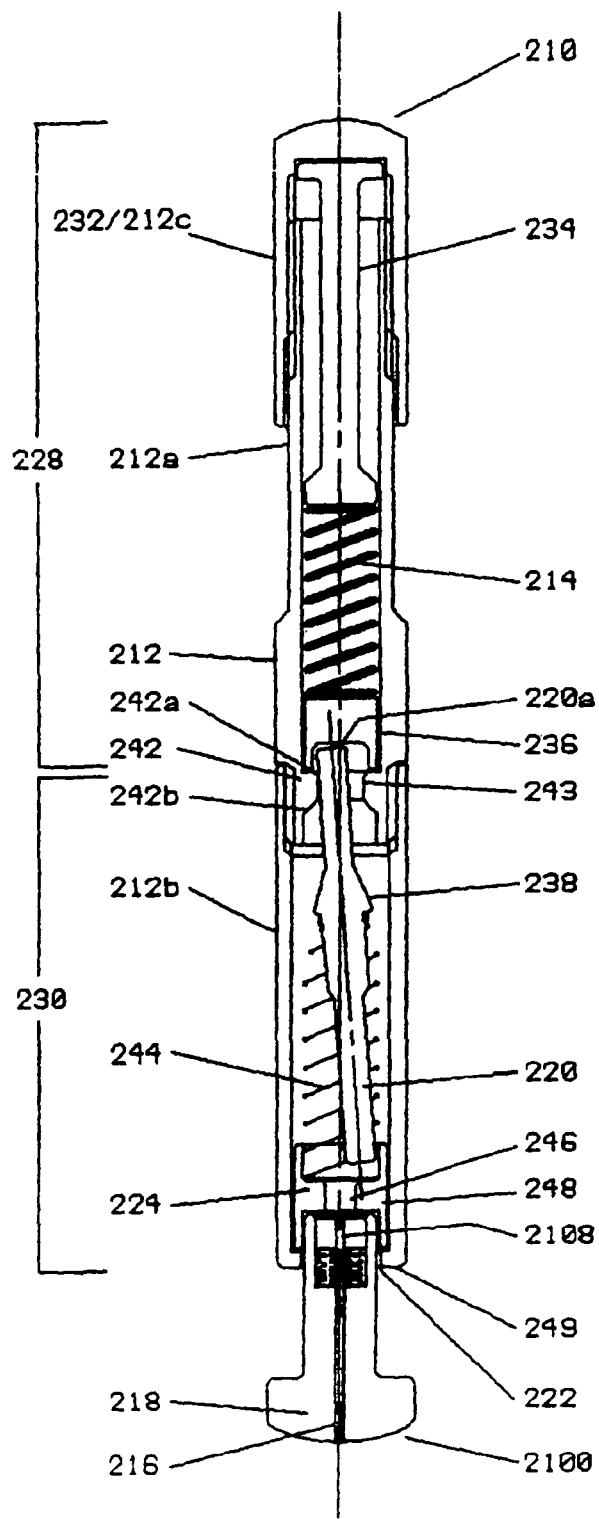
FIG. 17 is one embodiment of a reusable device according to one aspect of the invention with one embodiment of a packaged drug according to another aspect attached thereto, the device being shown pre-use.

The device illustrated in FIG. 17 is a (reusable) drug delivery device (210), with a packaged drug (2100) fitted thereto. It comprises very few components. They include i) a housing (212);
ii) a means (214) for generating a force capable of pushing a drug (216) from a packaging (218) into a human or animal body;
iii) a means (220) for transmitting said force to push the drug (216) from the packaging (218) into the human or animal body;
iv) a means (222) for receiving a packaged drug (2100);
v) a means (224) for priming the device; and
vi) a means (238,242b) for triggering the device.

In the embodiment shown the device is primed and triggered in a single action.

The delivery device (210) which may be absent of the packaged drug (2100) is spring powered. It can deliver the drug or a formulation containing a therapeutic compound (hereafter drug) in a solid, semi-solid or liquid form. By altering the form of the packaged drug (2100) the device can be used to either deliver drugs through a retractable needle (FIG. 20), or behind a "pioneer projectile" (FIGS. 19 and 21). It can also be used to deliver a solid drug splinter.

Looking at the device in more detail it comprises a number of components which are readily assembled and easily sterilised making manufacture cheap.

The body of the device comprises a three part housing (212) comprising a first housing component (212a) defining an upper barrel (228) which houses the force generating means (214), a second housing component (212b) defining a lower barrel (230) which houses the packaged drug (2100) and the means (220) for transmitting the force to push the drug (216) from its packaging (218). The first and second housing components (212a; 212b) connect to one another, and a third housing component (212c), which preferably takes the form of a screw cap (232), fits over the end of the first housing component to close off the upper barrel (228).

Within the upper barrel (228) is fitted the means (214) for generating the force capable of pushing the drug (216) from its packaging. In the embodiment shown this takes the form of a mechanical coil spring which can generate a force of from about 10-40 N, more preferably 15-35 N and most preferably 18-31 N. The spring is connected at its lower end to a spring follower (236) which is slidably mounted in the upper barrel (228). Above the spring is a compression bar (234) which provides a contact surface against which the spring can act. By screwing or unscrewing the cap (232) from the housing component (212a) the spring can be caused to compress or relax thereby providing a means for adjusting the force that can be generated by it. In FIG. 17 the spring is shown at minimum pre-load.

The upper barrel (228) and lower barrel (230) are separated from one another by a wall (242) with a communicating aperture (243) therein and it is on the upper surface (242a) of this wall that the spring follower (236) sits. The means (220) for transmitting the force generated by the spring takes the form of an impact hammer one end (220a) of which passes through the communicating aperture (243) where it contacts spring follower (236). In use the uppermost end (220a) of the impact hammer slides through the communicating aperture (243) pushing the spring follower (236) up the upper barrel (228) causing the spring to be compressed thus priming the device.

Within the lower barrel is housed not only the majority of the impact hammer (220), but a slewing spring (244) and a sliding piston (248) having an aperture (246) therein, such that the lower barrel can operatively communicate with the packaged drug (2100) which is secured to the device via the receiving means (222) provided at the devices lowermost end (249).

The slewing spring functions to draw the longitudinal axis of the impact hammer off centre (FIG. 18a) in the devices rest position. However, the hammer is adapted by way of a shaped shoulder region (238), (which in a preferred embodiment is substantially frustoconical, as illustrated) to be drawn into axial alignment with the aperture (246) in the sliding piston, against the action of the slewing spring (244), such that when it is fully primed the device automatically actuates. Accordingly the lowermost surface (242b) of the wall (242) is shaped to receive the shaped shoulder region (238) of the impact hammer and cause the impact hammer to be axially aligned with the aperture (246) in the sliding piston (248) such that it is driven by the spring (214) through the aperture (246) in the sliding piston (248) where it contacts a drive pin (2108) or other element causing the drug (216) to be pushed out of its packaging (218) into the human or animal. In contrast with the FIG. 17 embodiment it should also be noted that the end (220a) of the impact hammer graduates to a point (being substantially conical) and is seated in a similarly shaped recess (236a) in the spring follower (236). The shaping of the hammer end (220a) and the provision of the similarly shaped recess (236a) in the spring follower (236) further improves reliability of actuation.

Figure 18A:
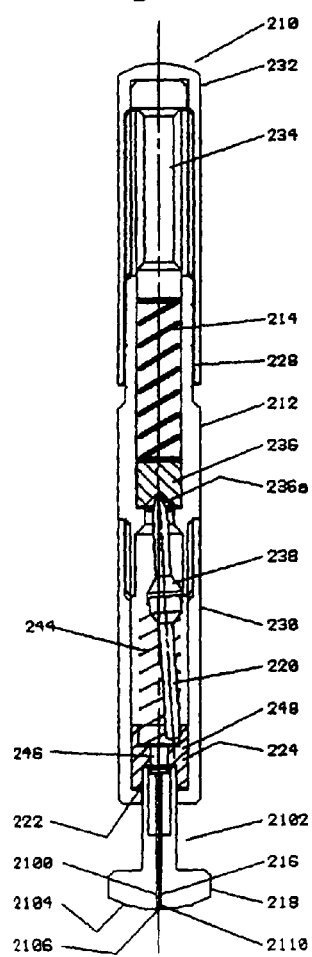
Figure 18B:
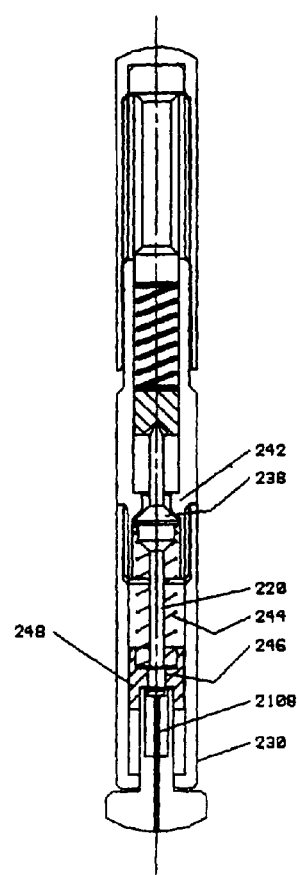
Figure 18C:
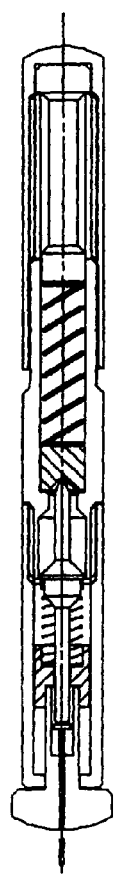

By comparison of FIG. 18a with FIGS. 18b and c it will be apparent that once a packaged drug (2100) has been attached to the lower most end (249) of the device (210) it can be actuated by a user holding the device about it's housing (212) and pressing the device (210) firmly against the patients skin. This causes first the skin to be tensioned and then the packaged drug (2100) slides up the lower chamber (230) pushing the piston (248) which in turn pushes the impact hammer (220). As it does so the upper end (220a) of the impact hammer pushes against the spring follower (236) causing the spring (214) to be compressed until the necessary drive force is reached. This is at the point illustrated in FIG. 18b. At this point the shaped shoulder region. (238) is drawn into the shaped lowermost surface (242b) of wall (242), the action of the slewing spring (244) is countered, the spring (214) is fully charged and the impact hammer (220) axially aligned with the aperture (246) in the sliding piston (248) such that it will automatically actuate, the spring (214) forcing the impact hammer (220) through the aperture (246) in the piston (248) causing it to push the drive pin (2108) which in turn, depending on the mechanism employed in the packaged drug (2100) (see FIGS. 19 to 21) causes the drug to be dispensed into the human or animal. Significantly the longitudinal axis of the impact hammer can't be aligned with the aperture (246) in the sliding piston (248) until it reaches the set actuating force which is set to coincide with the point at which the shaped shoulder region (238) contacts the shaped lowermost surface (242b) of wall (242) thus providing a safety mechanism against accidental actuation. When it reaches this point triggering is automatic and the device is actuated (FIG. 18c).

It should be noted that on actuation the hammer moves only a short distance, less than 10 mm, more preferably less than 5 mm and typically about 3 mm before impacting the drive pin and therefore moves (say) approx 5 mm before the pioneer projectile strikes the skin. This means that the maximum force and impact are all in the first few millimeters of travel, when the maximum force is required to pierce the skin. Through the rest of the delivery, the force is reducing as the main spring power is diminishing and also the slewing spring is being compressed (FIG. 18c). This means that the force tapers off during the second half of the delivery when less force is required.

Therefore the force profile through the whole delivery matches the requirements i.e. a high force and impact to pierce the skin and then a reduced force to push the injectate into the skin.

In the case of a reusable device the packaged drug is removed from the device and discarded. The slewing spring will assist in this action. As the packaged drug (2100) is removed from the device the slewing spring (244) acts to draw the impact hammer (220) so that it is not axially aligned with the aperture (246) in the piston (248) and the device (210) is ready to receive a new packaged drug.

Such a device can be used to dispense a drug in a variety of different forms depending on how it is packaged.

To demonstrate the versatility of the device three different designs (FIGS. 19, 20, and 21) of packaged drug (2100) are illustrated as suitable for use with the device. All three embodiments illustrate the dispensing of a single dose but the skilled man will appreciate that multi-doses could also be dispensed simultaneously or sequentially with the device of the invention. Similarly, the device could be produced in a pre-primed form with the packaged drug forming an integral part of the device.

Referring to FIG. 19, in one embodiment the packaged drug (2100) takes the form of an end piece which is adapted to be slidably mountable in the device (210). The packaging (218) takes the form of a two-piece housing (218a, 218b), thereby simplifying construction and assembly. A first housing element (218a) is the shape of a hollow inverted "T" and comprises a region (2102) (the stem of the "T") which serves in use to slidably engage the device (210) allowing the packaged drug to slide up the lower chamber (230) of the device (210), and a "cross piece" against which the second element (218b) abuts. A central channel (2106a) runs through the middle of the stem exiting at the crosspiece. The second element (218b) comprises an end (2104) which is shaped to tension the skin. The second element (218b) is also substantially the shape of an inverted T and has a channel (2106b) running down the centre axis of the inverted T. The respective channels (2106a, 2106b) communicate with one another to form a single channel (2106) which runs right through the packaging (218). The channel (2106b) houses a pioneer projectile (2110) and the drug (216) or a drug splinter (effectively 2110, 216), the skin contacting end of which is set a few millimeters in from the skin tensioning surface of the device to ensure it is moving at the requisite speed when it contacts the skin. It also houses the lower end (2108b) of the drive pin (2108). At the end remote from the skin tensioning surface the channel (2106b) opens out to house a resilient member e.g. a spring (2114). The placing of a resilient member under the head (2108a) of the drive pin allows the drive pin to be withdrawn back into the housing immediately after actuation. The drive pin (2108) is slidably mounted in the channel (2106) so that when the head is depressed by the hammer of the device the drive pin moves down the channel pushing the pioneer projectile and drug (2110, 2216) from the channel (106b) into the human or animal body. The pioneer projectile (2110) and drug (216) are held in place in the channel (2106b) by, for example, a breakable membrane (not shown) or appropriate frictional means e.g. one or more markings or splines on either the pioneer projectile, drug and or channel (2106b) surface.

The packaged drug illustrated in FIG. 19 is suitable for the injection of a "contained" drug behind a pioneer projectile which can penetrate the skin and create a channel into which the drug is pushed as described. This type of packaged drug is also suitable for the administration of drug splinters or rods of a solid therapeutic compound which have a sharp tip as per WO 94/22423. The therapeutic compound or therapeutic compound and tip are initially located in the channel (2106) of the packaging (218). The distal end (2108b) of the drive pin may or may not be in contact with the uppermost end of the therapeutic compound prior to actuation. When the drive pin head (2108a) is struck by the impact hammer the drive pin (2108) pushes the therapeutic compound (and pioneer projectile, if included) into the target tissue.

The end of the drive pin may just penetrate the outer layers of the skin to ensure that the therapeutic compound is completely delivered into the skin. Alternatively, the packaged drug may include a short rod (or rods) of a placebo or pharmaceutical compound between the end of the drive pin and the therapeutic compound, which can be used to push the therapeutic compound fully into the skin. In this case it would not matter if the placebo rods entered the skin but it would ensure that the drive pin did not have to penetrate the skin. The benefits of this are that the drive pin would not be left protruding from the packaged drug following the administration and would not be contaminated with bodily fluids and it would therefore not pose a health risk in terms of disposal. An alternative is to include a piece of rubber or foam, or as illustrated a light spring (2114), under the head (2108a) of the drive pin to ensure that the tip of the drive pin is withdrawn into the spent packaging after administration.

FIG. 20 illustrates an alternative design of a packaged drug for use with a device according to the invention. The packaged drug comprises a two piece housing (218a, 218b) which is identical to that of the FIG. 19 embodiment. This simplifies manufacture as the housing components can be used for a packaged drug which is solid (as per the FIG. 19 embodiment) or one which is liquid. In order to be adapted to dispense a liquid a needle (2112) sits in the channel (2106), it's lower end (2112b) being in the channel (2106b) of housing component (218b) and its upper end (2112a) extending into the channel (2106a) of housing component (218b). The needle (2112) is obliquely cut at both ends to provide sharp points. Attached to the upper end (2112a) of the needle is a support plate (2113) on which is seated a resilient or compressible spacer (2126) which extends above the tip of the upper end (2112a) of the needle. Seated on the spacer (2126) immediately above the tip of the needle (2112) is a liquid drug containing receptacle (2120). The receptacle comprises one or more side walls (2121) and a puncturable base (2122) which together define a receptacle cavity which is filled with the drug (216) through an opening (2124). The receptacle is sealed by a drive pin or element (2108) which sits in the receptacle opening (2124).

In use the hammer of the drug delivery device contacts the drive element head (2108a) causing the receptacle to be pushed down the channel (2106a) of the housing element (218a). The spacer (2126) is compressed causing the needle to puncture the base (2122). Consequently the needle (2112) is filled by some of the drug contents (216) of the receptacle thereby expelling air from the needle prior to piercing of the skin and delivery of the drug. The force exerted on the support plate (2113) forces the needle into the skin where the liquid drug contents (216) drain into the human or animal through the tract formed by the needle (2112). As the user of the device removes the device from the skin, the drug package is pushed substantially out of the end of the device by the action of the slewing spring, and the needle is withdrawn into the drug package by the action of the spring (2114).

In yet a further embodiment, and as illustrated in FIG. 21 there is a packaged drug (2100) which is adapted to hold a drug (216) in any state, liquid, semi solid or solid. As in the previous embodiments the housing (218) preferably takes the form of a two piece housing (218a, 218b) although in this case the housing elements are shaped differently. In channel (2106b) of the second housing element (218b) is housed a pioneer projectile (2110) and the lowermost part of a drug containing receptacle (2120) in the form of a thin walled metal tube which is sealed with a breakable membrane (2122). The tube terminates at it's uppermost end in a lip (2121) on which rest a pair of flexible arms (2128) of a drive element (2108). The receptacle is sealed by the drive element (2108). At the end remote from the skin tensioning surface of the second housing element (218b) is a ramped surface (2130). The uppermost part of the drug containing receptacle (2120) and the drive element (2108) sit in a cavity between the housing elements (218a, 218b) and which can be considered an extension of channel (2106a) formed in the first housing element (218a). The end (2104) in this embodiment is particularly well suited to skin tensioning and includes an annular ring (2105) located immediately about the channel (2106) exit. The annular ring in this embodiment is about 3 mm in diameter (including the channel which is about 1 mm in diameter) and depth. By way of comparison the end (2104) has a diameter of about 16 mm. The depth and width need not be 3 mm by 3 mm but should generally be in the range 1.5 mm to 6 mm. Any more than this and it may cause pain and bruising and any less than this and it may not adequately tension the skin. This annular ring which may be a whole ring or a broken ring comprising a number of projecting elements disposed in a substantially annular fashion about the channel exit could be a feature of any embodiment. To simplify construction in this embodiment the drive pin head (2108a) is produced as separate component to the lower and elongate end (2108b) of the drive pin.

In use the hammer of the drug delivery device contacts the drive element head (2108a) causing the receptacle to be pushed down the channel (2106b) as a consequence of the force exerted by the flexible arms (2128) of the drive element (2108) against the lip (2121) of the receptacle (2120). This causes the pioneer projectile (2110) to be pushed into the patient. Once the pioneer projectile has entered the patient the flexible arms (2128) of the drive element (2108) contact the ramp surface (2130) of the second housing element (218b) and are caused to flex apart and ride over the lip (2121) and/or snap. As a consequence the lower part (2108b) of the drive element is able to move down the receptacle (2120) pushing the drug (216) contents out into a tract formed by the pioneer projectile (2110). Preferably the end of the receptacle which takes the form of a thin walled tube just enters the skin before the drug is delivered. This ensures that if a liquid drug is used the drug follows the pioneer projectile into the skin rather than escaping along the skin surface.

The main advantage of the FIG. 21 embodiment is for the injection of liquids as it ensures that the liquid is contained during the administration and is guided by the thin walled metal tube into the target tissue. However, the drug contents need not be restricted to liquids.

A feature of the device illustrated which further distinguishes it from other hand powered systems is that the force generated by the spring is the delivery force and there is substantially no additional force generated by the operator due to the gradual priming and instantaneous actuation when the device reaches the delivery force set.

In contrast devices which include a break tab or other snap means to actuate the device can't have the force carefully controlled and as a consequence the greater the force exerted by the user the greater the velocity of impact by the drug with the skin.

With the system detailed in this application the hand force compresses the main spring to a preset point at which the drug package is inserted to virtually its maximum point within the device. At this point the actuation takes place and the predetermined spring strength delivers the drug. Any extra force by the hand is dissipated over the whole of the area of the end of the device.

An alternative way of viewing this is to consider the skin as a sponge. In devices utilising snap tabs, when the snap tabs are broken all the force by the hand is pushing the drug and the resilience of the skin will start to push the bottom half of the device (part not held in hand) back towards the hand. This may result in a less good seal with the skin and, in theory, if the hand force stops immediately the snap tabs are broken then the drug would never be pushed from the device - they rely on the inertia in the hand to make the injection. In practice this means that the user pushes and pushes and then suddenly the tabs break and the device is pushed into the target possibly causing pain and bruising with the device. In the present injection the skin is compressed by a steady hand force. At the point of actuation the main spring controls the delivery of the drug and the hand maintains (but does not suddenly increase) the force on the skin to ensure a good contact with the skin. If at any point before actuation the sensation on the skin is painful then the injection site can be altered or the injection aborted rather than causing further pain and/or bruising.

Devices of the type described have been demonstrated by the applicant to be capable of delivering a drug as demonstrated by the following examples:

EXAMPLES

Initial experiments were carried out with non pharmaceutical materials to demonstrate the delivery concept. These experiments comprised the following:

Example 1

Drug Splinters

A rod of 0.9 mm diameter pencil lead was broken to lengths of approximately 6 mm and a point was sanded on one end of each length and a flat on the other to create solid splinters. The splinters were placed in the drug package shown in FIG. 19 and successfully administered to pig skin using a prototype delivery system.

Example 2

Pioneer Projectile Followed by a Solid Rod

The same pencil lead detailed in example 1 above was cut into short lengths of approximately 3 mm in length. These had a point sanded on one end and a flat on the other end to create pioneer projectiles. Further rods of the same pencil lead were cut at approximately 4 mm in length and had both ends sanded flat. When a pioneer projectile and a solid rod were placed in a drug package as shown in FIG. 19 they were successfully administered to pig skin using a prototype delivery system.

Example 3

Pioneer Projectile Followed by a Soft Rod

A soft rod of wax was extruded through a die and rods of approximately 4 mm in length were cut with a flat at each end. Further sections were cut with a point at one end and a flat at the other end. When a pointed section (identical in shape and size to the splinter used in example 1) was administered to pig skin using a drug package as shown in FIG. 19 the wax did not pierce the skin but was flattened on the skin surface. When a rod of the same waxy material was placed behind a pioneer projectile used in example 2 and administered to pig skin using a drug package as shown in FIG. 19 then both the pioneer projectile and the waxy material were successfully delivered into the tissue. The wax material used for this experiment could easily be squashed between a finger and a thumb.

Example 4

Pioneer Projectile Followed by Solid Beads.

Beads of diameters 0.5-0.75 mm were placed in a drug package, as shown in FIG. 19, behind a pioneer projectile as detailed in example 2. The pioneer projectile and all the beads were successfully administered to pig skin using a prototype delivery system.

The experiments outlined above demonstrated that a range of different materials could be delivered behind a solid pioneer projectile. Ideally it is preferred that the pioneer projectile is manufactured from pharmaceutical grade compounds that will dissolve in the target tissue. Two processes have been used to produce such pioneer projectiles as outlined below:

Example 5

A hot melt of sugars is produced which can then be moulded into the correct form for a pioneer projectile or extruded to produce long rod. If an extrusion process is used then the pioneer projectiles can be cut to shape from the soft extrudate or the sharp ends of the pioneer projectile can be formed when the extrudate has solidified. This process produces a material similar to a boiled sweet which can be very hard and incorporate a sharp point on one end.

Example 6

A mix of powders is produced using pharmaceutical grade sugars together with a hardening agent such as polyvinylpyrolidone (PVP). The powder blend is extruded through a die to produce a long rod of the compound. Some blends require a lubricant to facilitate the extrusion and binding process such as water or ethanol. The pioneer projectiles are formed by cutting the long rod into short sections. This process can be facilitated by using a hot knife. If necessary, the point or flat end of the pioneer projectile can be created by sanding or filing a short rod of the extrudate.

We claim:

1. A drug delivery device comprising a housing, said housing comprising:
   i) an upper barrel at one end of the device which houses a generator of a force capable of pushing a drug from a packaging into a human or animal body; and
   ii) a lower barrel, at the end remote from the upper barrel, which houses:
      a) a packaged drug assembly;
      b) a striker to cause the drug to be pushed from the packaged drug assembly;
      c) a receiver for receiving the packaged drug assembly;
      d) a trigger device; and
   said lower barrel being in operative communication with said upper barrel;
   and wherein the packaged drug assembly and striker are slidably mounted in the device, and pushing the device against the skin with sufficient force causes the packaged drug assembly and striker to slide up the lower barrel and the device to be primed and actuated.

2. A drug delivery device as claimed in claim 1 wherein the generator is capable of generating a force of from 10-40N.

3. A drug delivery device as claimed in claim 1 wherein the transmitter causes the drug to be pushed from the packaging at less than 10m/s.

4. A drug delivery device as claimed in claim 1 wherein said packaged drug assembly is slidably disposed in the receiver.

5. A drug delivery device as claimed in claim 1 wherein the packaged drug assembly is slidably disposed in the lower barrel and comprises a a packaged drug assembly housing having a channel running there through in which is disposed a drive pin, a skin piercing element and the drug; said packaged drug assembly housing further comprising
   a region allowing the packaged drug assembly to be slidably mounted to the drug delivery device at the receiver.

6. A drug delivery device as claimed in claim 5 wherein the skin piercing element is a pioneer projectile, a syringe needle or the head of a drug splinter.

7. A drug delivery device as claimed in claim 5 wherein the drive pin or other element has a flat or enlarged head.

8. A drug delivery device as claimed in claim 5 further comprising a resilient element below or otherwise in association with the drive pin or other element to ensure the drive pin is withdrawn after use.

9. A drug delivery device as claimed in claim 5 wherein the packaged drug assembly further comprises an end adapted to engage and tension the skin.

10. A drug delivery device as claimed in claim 1 wherein the generator is a spring.

11. A drug delivery device as claimed in claim 10 wherein the spring is a coil or gas spring.

12. A drug delivery device as claimed in claim 10 wherein the force generated by the spring is adjustable.

13. A drug delivery device as claimed in claim 10 further comprising a sliding piston, wherein the packaged drug assembly acts against the sliding piston and causes the spring to be tensioned and the device primed.

14. A drug delivery device as claimed in claim 1 wherein the trigger device comprises a region of the striker that is shaped to fit a correspondingly shaped surface in a wall separating the upper and lower barrels defined by the housing and wherein the striker is aligned to strike a drive pin in the packaged drug assembly on actuation.

15. A drug delivery device as claimed in claim 14 wherein the device comprises a slewing spring, a sliding piston having an aperture therein, all housed in the lower barrel and the device is triggered by the sliding of the piston up the lower barrel until the shoulder region of the striker engages the shaped surface and aligns the striker with the aperture in the sliding piston such that the striker moves down the aperture under the action of the generator.

16. A device as claimed in claim 15 wherein the action of pushing the packaged drug assembly up the lower barrel with sufficient force causes the sliding piston to move up the lower barrel thereby causing the striker to be pushed up the lower barrel out of a first position in which it is not axially aligned with the aperture in the sliding piston which operatively communicates with the packaged drug assembly and at the same time acts on a spring follower in the upper barrel causing the spring to be compressed and the device primed such that when the required delivery force is generated the striker is axially aligned with the aperture of the sliding piston and is thus actuated such that the spring acts through the spring follower and striker upon the drive pin in the packaged drug assembly to deliver the drug into the human or animal body.

17. A drug delivery device as claimed in claim 1 wherein the striker comprises a substantially frustoconical shoulder region which engages a substantially frustoconical surface in the wall separating the upper and lower barrels defined by the housing.

18. A drug delivery device as claimed in claim 1 wherein the device is primed and actuated by a single action.

19. A device as claimed in claim 1 wherein the device is primed and actuated by two separate actions.

20. A drug delivery device as claimed in claim 1 wherein the upper barrel and lower barrel are formed as separate components.

21. A drug delivery device as claimed in claim 1 wherein the drug is in a contained form.

22. A drug delivery device as claimed in claim 21 wherein the drug is either: a liquid contained by a membrane; a liquid with a viscosity of at least 500 centipoises, a semi solid, a paste, a gel or a solid.

23. A drug delivery device as claimed in claim 1 wherein the packaged drug assembly is an integral part of the device.

24. A drug delivery device as claimed in claim 1 in which the device and/or packaged drug assembly is sealed in a foil pouch or the like to prevent ingress at: for example, moisture, oxygen, light, bacteria or other drug degrading or contaminating agents.

25. A drug delivery device as claimed in claim 1 further comprising a positive lock retention system to ensure the packaged drug assembly does not come away from the device under gravity yet is free to slide up the device.

26. A single use drug delivery device as claimed in claim 1 wherein the
packaged drug assembly forms an integral part of the device.

27. A drug delivery device as claimed in claim 1 wherein the packaged drug assembly is disposable.

28. A drug delivery device as claimed in claim 1 wherein the striker is in a non-axially aligned position prior to device actuation.

29. A drug delivery device as claimed in claim 1 wherein prior to actuation the striker is held in a first non-axially aligned position and the sliding of the packaged drug assembly up the lower barrel causes the striker to move into a second, axially aligned position to actuate the device.

30. A drug delivery device as claimed in claim 1 further comprising a slewing spring that holds the striker in a non-axially aligned position prior to actuation and returns the striker to the non-axially aligned position after actuation.

31. A packaged drug assembly, for use with the drug delivery device of claim 1, comprising a packaged drug assembly housing having a channel running there through and in which is disposed a drive pin, a skin piercing element, and a drug, said packaged drug assembly housing further comprising
   i) a region allowing the packaged drug assembly to be slidably mounted to the drug delivery device; and
   ii) an end adapted to engage and tension the skin.

* * * * *